United States Patent [19]

Tsuchiya et al.

[11] 4,113,864
[45] Sep. 12, 1978

[54] PHOSPHOROTHIOLATE PESTICIDAL COMPOSITION

[75] Inventors: Hiroshi Tsuchiya, Ashiya; Kunio Mukai, Nishinomiya; Akio Kimura, Takarazuka; Hiroshi Taya, Minoo; Keimei Fujimoto, Kyoto; Toshiaki Ozaki; Sigeo Yamamoto, both of Toyonaka; Taizo Ogawa; Tadashi Ooishi, both of Minoo; Yositosi Okuno, Toyonaka, all of Japan

[73] Assignee: Sumitomo Chemical Company, Limited, Osaka, Japan

[21] Appl. No.: 768,875

[22] Filed: Feb. 15, 1977

Related U.S. Application Data

[60] Division of Ser. No. 415,682, Nov. 14, 1973, Pat. No. 4,028,438, which is a continuation of Ser. No. 8,434, Feb. 3, 1970, abandoned, which is a continuation-in-part of Ser. No. 728,353, May 10, 1968, abandoned.

[30] Foreign Application Priority Data

| May 17, 1967 [JP] | Japan | 42-31645 |
| Sep. 8, 1967 [JP] | Japan | 42-57677 |
| Sep. 11, 1967 [JP] | Japan | 42-58536 |
| Sep. 12, 1967 [JP] | Japan | 42-58859 |

[51] Int. Cl.² ................... A01N 9/00; A01N 9/36
[52] U.S. Cl. ................... 424/225; 424/200; 424/216; 424/219
[58] Field of Search ................ 424/200, 216, 219, 225

[56] References Cited

U.S. PATENT DOCUMENTS

| 3,641,221 | 7/1972 | Schrader et al. | 260/964 |
| 3,839,511 | 10/1974 | Kishino et al. | 260/964 |
| 4,028,438 | 6/1977 | Tsuchiya et al. | 260/948 |

Primary Examiner—Allen J. Robinson
Attorney, Agent, or Firm—Stevens, Davis, Miller & Mosher

[57] ABSTRACT

Phosphorothiolates represented by the formula,

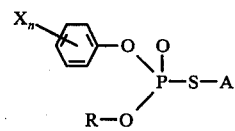

wherein R is an alkyl; A is an alkyl, haloalkyl, alkenyl, alkinyl, alkylthioalkyl, phenylthioalkyl, phthalimidoalkyl or phenylalkyl; X is hydrogen, a halogen or an alkyl; and $n$ is an integer of 1 to 5, are obtained by (1) reacting sodium or potassium hydrosulfide with a compound represented by the formula,

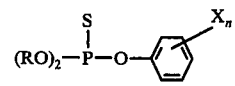

wherein R, X and $n$ have the same significances as mentioned above, to prepare a thiophosphate represented by the formula,

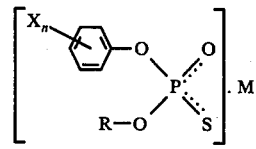

wherein R, X and $n$ have the same significances as mentioned above; and M is an alkali metal, and then (2) reacting said thiophosphate with a halide represented by the formula,

Y — A wherein A has the same significance as mentioned above; and Y is a halogen.

The phosphorothiolates have insecticidal and fungicidal activities.

27 Claims, No Drawings

PHOSPHOROTHIOLATE PESTICIDAL COMPOSITION

This is a division of application Ser. No. 415,682 filed Nov. 14, 1973, now U.S. Pat. No. 4,028,438, which in turn is a continuation of Ser. No. 8,434, filed Feb. 3, 1970, now abandoned, which in turn is a continuation-in-part of Ser. No. 728,353, filed May 10, 1968, now abandoned.

This invention relates to novel phosphorothiolates having insecticidal and fungicidal activities, to a process for preparing the same, and to insecticidal and fungicidal compositions containing the same.

Further the present invention relates to novel thiophosphate, and method for producing the same.

At present, organophosphorous compounds such as O,O-dimethyl-O-4-nitrophenylphosphorothioate and organomercury preparations are extensively used as insecticides and fungicides. However, the use thereof has come into question due to their toxicities to mammals. Further it is difficult to control agricultural injurious insects, sanitary injurious insects and agricultural fungi by using a composition containing only one active ingredient.

The present inventors found that novel phosphorothiolates having insecticidal activities capable of completely and advantageously controlling agricultural injurious insects and sanitary injurious insects have been produced by reacting a novel thiophosphate with a halide. As to insecticidal activities, these phosphorothiolates were as strong as O,O-dimethyl-O-3-methyl-4-nitrophenyl phosphorothioate and O,O-dimethyl-O-4-nitrophenyl phosphorothiolate and were successfully applicable to a wide variety of injurious insects. That is, they not only had prominent effects on rice crop injurious insects such as rice stem borers, leaf hoppers and plant hoppers but also showed marked activities towards injurious insects belonging to the order of Coleoptera, Lepidoptera and Diptera and towards plant parasitic nematodes. The characteristics of the above phosphorothiolates are such that they showed towards mites as high as several times the effects of existing mitecides, and that they displayed marked activities towards beetles such as red bean beetles and rice weevils, as well.

Further, the present inventors found that the said phosphorothiolates had effects on various rice diseases and, particularly on rice blast, and that they had more excellent effects than those of commercially available fungicides. In addition, they showed prominent effects of controlling Helminthosporium leaf spot and rice sheath blight.

These phosphorothiolates have both insecticidal and fungicidal actions and hence can control both injurious insects and plant diseases. This is an excellent feature which has never been attained heretofore.

The abovve-mentioned phosphorothiolates, however, show no such strong and acute toxicities as seen in O,O-dimethyl-O-4-nitrophenyl phosphorothioate, and contain no such poisonous heavy metal as mercury, and therefore are low toxic. Accordingly, they have great advantages in application.

SUMMARY OF THE INVENTION

An object of the present invention is to provide novel phosphorothiolates having both insecticidal and fungicidal activities.

Another object is to provide a process for preparing novel phosphorothiolates having insecticidal and fungicidal activities.

A further objject is to provide novel thiophosphates and a process for producing the same.

Furthermore it is an object of the present invention to provide insecticidal and fungicidal compositions containing novel phosphorothiolates.

Other objects will become clear from the description that follows.

In order to achieve the above objects, the present invention provides phosphorothiolates represented by the formula,

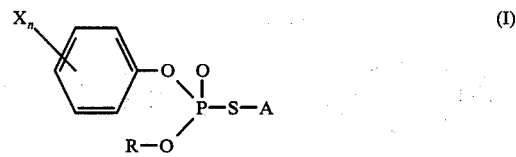

wherein R is an alkyl having up to 5 carbon atoms; A is an alkyl having 3 or 4 carbon atoms, haloalkyl having up to 3 carbon atoms, alkenyl having up to 4 carbon atoms, alkinyl having up to 4 carbon atoms, alkylthioalkyl having up to 6 carbon atoms, phenylthioalkyl having up to 9 carbon atoms, phthalimidoalkyl having up to 11 carbon atoms or phenylalkyl having up to 10 carbon atoms; X is hydrogen, a halogen or an alkyl having up to 5 carbon atoms; and $n$ is an integer of 1 to 5.

The present invention further provides a process for preparing phosphorothiolates represented by said formula [I], characterized by reacting a thiophosphate represented by the formula,

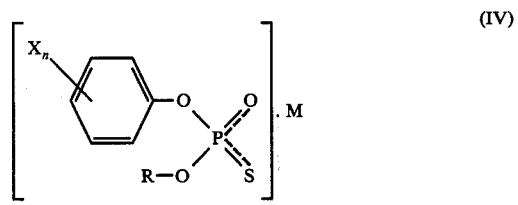

wherein R, X and $n$ have the same significances are mentioned above; and M is an alkali metal, with a halide represented by the formula,

wherein Y is a halogen; and A has the same significance as in the case of formula [I].

Furthermore the present invention provides thiophosphates represented by the formula [IV].

Still further the present invention provides a process for producing thiophosphates represented by the formula [IV], characterized by reacting an O,O-dialkyl-O-phenylphosphorothionate represented by the formula,

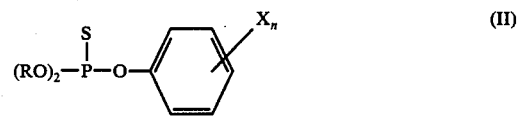

wherein R, X and $n$ have the same significances as mentioned above, with an alkali hydrosulfide represented by the formula,

M . SH    [III]

wherein M has the same significance as mentioned above, to prepare a thiophosphate represented by the aforesaid formula [IV].

The present invention still further provides a process for producing phosphorothiolates represented by said formula [I], characterized by reacting an O,O-dialkyl-O-phenylphosphorothionate represented by the formula,

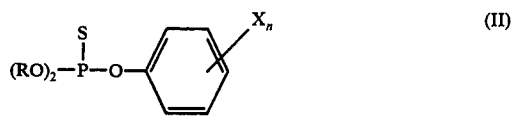

wherein R, X and $n$ have the same significances as mentioned above, with an alakli hydrosulfide represented by the formula,

M . SH    [III]

wherein M has the same significance as mentioned above, to prepare a thiophosphate represented by the aforesaid formula [IV], and then reacting said thiophosphate with a halide represented by the aforesaid formula [V].

The invention still further provides an insecticidal and fungicidal composition comprising an effective insecticidal and fungicidal amount of a compound represented by the aforesaid formula [I], and an inert carrier.

All the phosphorothiolates represented by the formula [I] and all the thiophosphates represented by the formula [IV] are novel compounds.

In the present invention, the preparation of the phosphorothiolates of the formula [I] by reaction of the thiophosphates of the formula [IV] with the halides of the formula [V] is carried out in the following manner:

The thiophosphate of the formula [IV] is added to a solvent. To this reaction mixture is added the halide of the formula [V], and the mixture is allowed to react. In this reaction, the order of addition is not so important. The halide is used in an amount of 0.9 to 1.5 moles per mole of the thiophosphate. The solvent may be freely selected from common solvents. Generally, however, solvents relatively high in polarity such as, for example, water, alcohols, alkoxyalcohols, ketones, dimethylformamide, dimethyl sulfoxide, acetonitrile, etc. give favorable results, and the use of solvents capable of dissolving both the starting materials, i.e. thiophosphates and halides, is preferable. As the thiophosphate, any of those prepared according to the method described afterwards may be used, regardless of whether they have been isolated or not. The conditions of the above condensation reaction greatly vary depending on the kind of starting materials and solvent employed. Generally, however, the reaction is effected at room temperature to about 150° C. for a period of 30 minutes to 10 hours. If desired, the halide, which is one starting material, is used in excess and is reacted with the other starting material thiophosphate, without using solvent, whereby the yield is increased, in some cases.

After the condensation reaction, the reaction product is subjected to ordinary after-treatments to obtain the desired phosphorothiolate of the formula [I].

Several examples of typical phosphorothiolates belonging to the present invention are shown below.

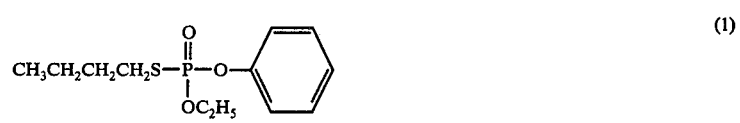

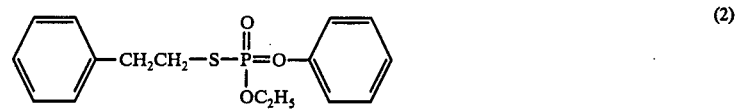

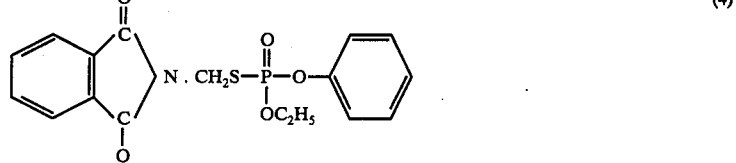

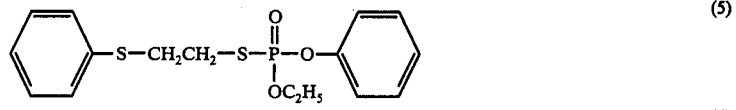

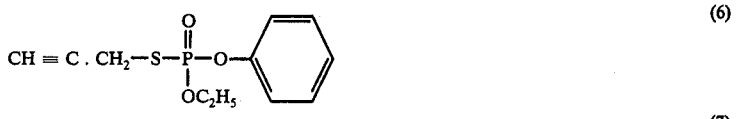

-continued
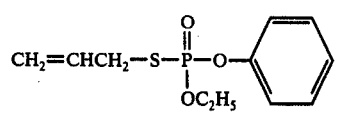 (8)
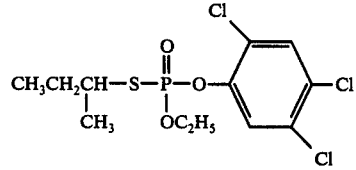 (9)
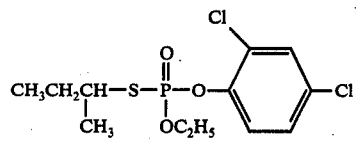 (10)
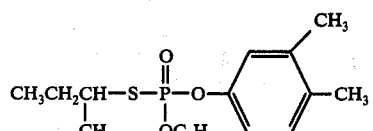 (11)
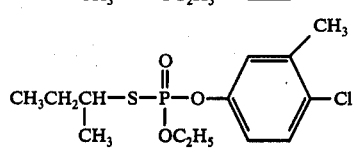 (12)
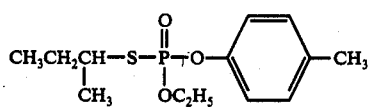 (13)
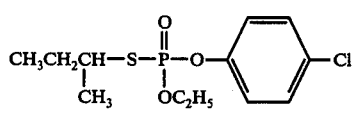 (14)
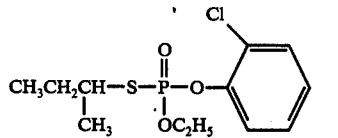 (15)
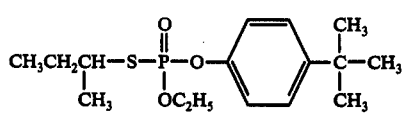 (16)
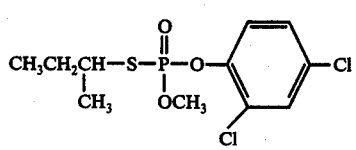 (17)
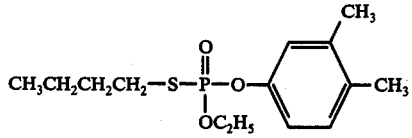 (18)
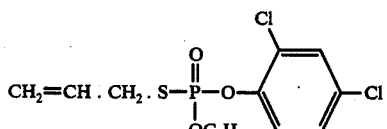 (19)
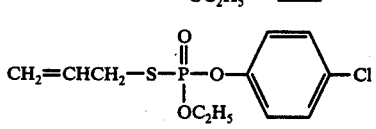 (20)

-continued
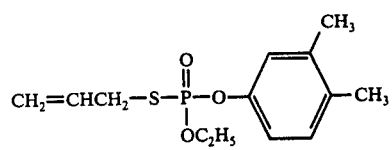 (21)
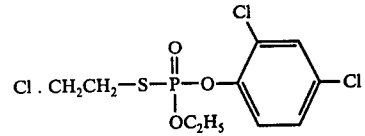 (22)
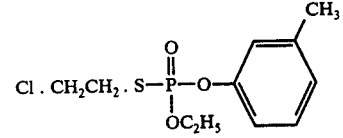 (23)
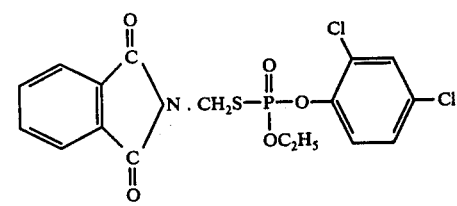 (24)
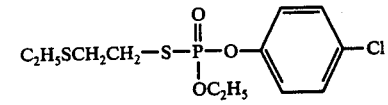 (25)
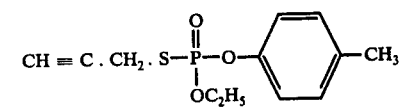 (26)
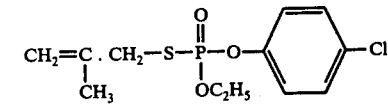 (27)
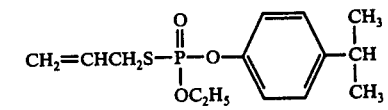 (28)
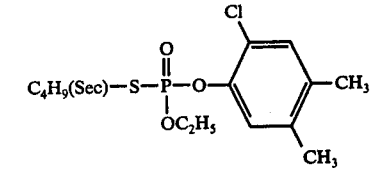 (29)
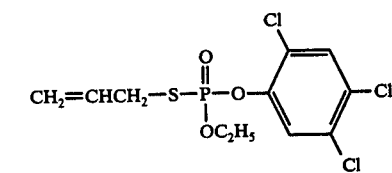 (30)
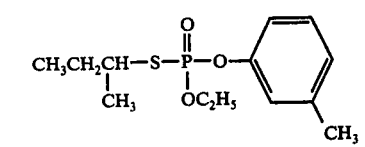 (31)
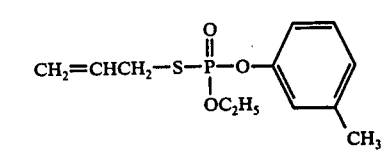 (32)

-continued
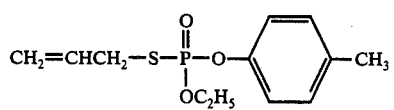 (33)
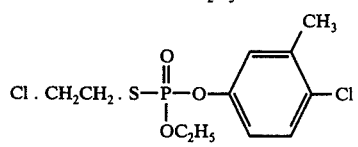 (34)
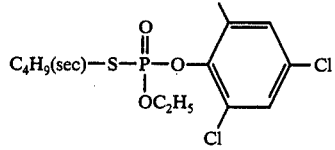 (35)
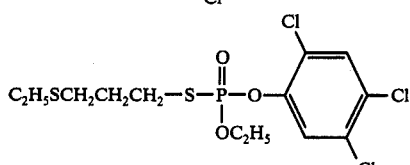 (36)
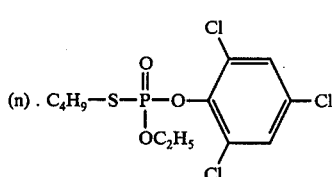 (37)
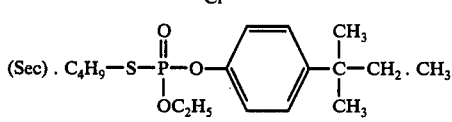 (38)
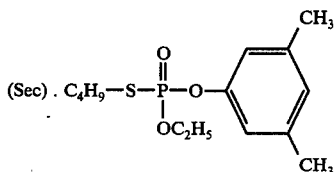 (39)
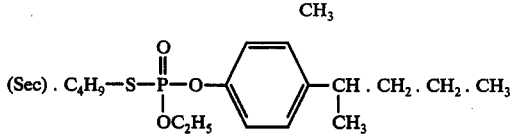 (40)
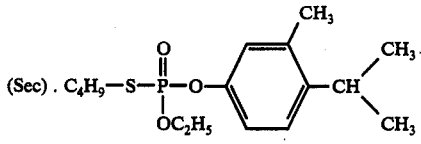 (41)
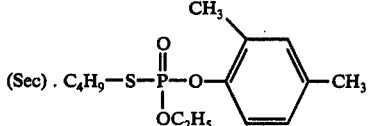 (42)
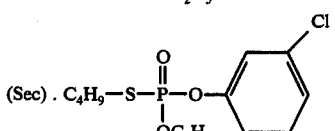 (43)
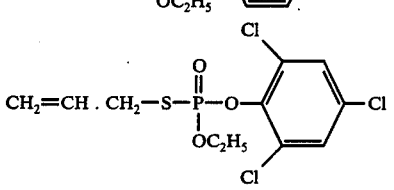 (44)

-continued
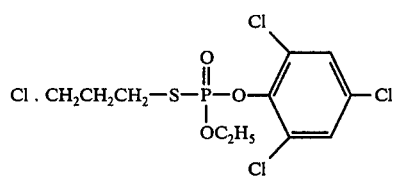 (45)
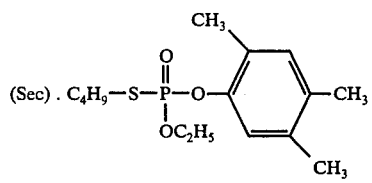 (46)
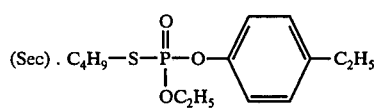 (47)
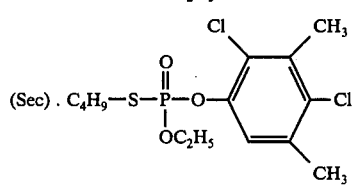 (48)
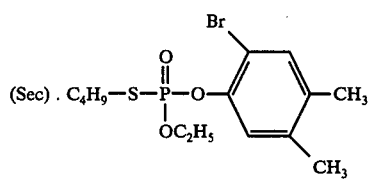 (49)
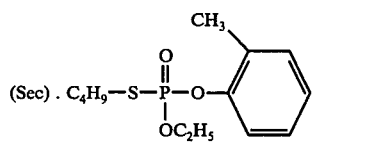 (50)
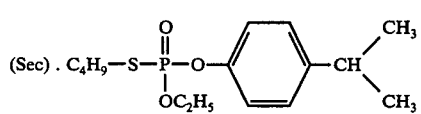 (51)
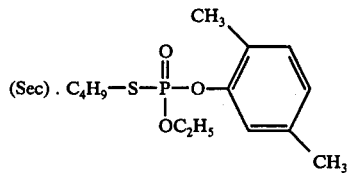 (52)
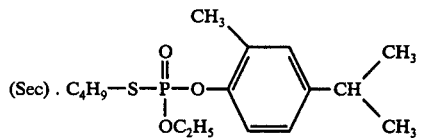 (53)
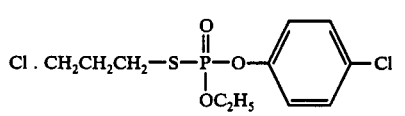 (54)
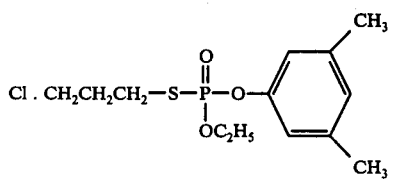 (55)

-continued
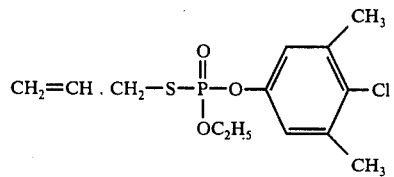 (56)
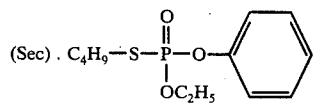 (57)
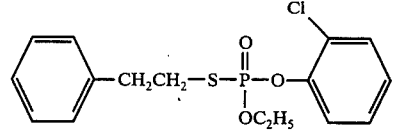 (58)
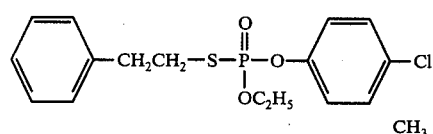 (59)
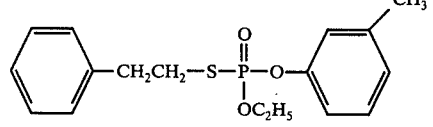 (60)
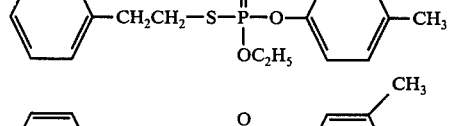 (61)
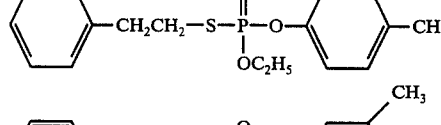 (62)
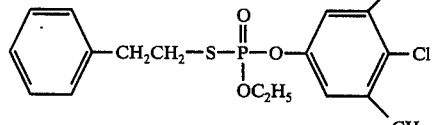 (63)
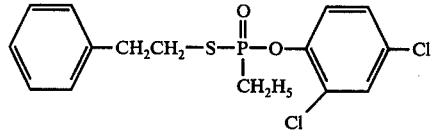 (64)
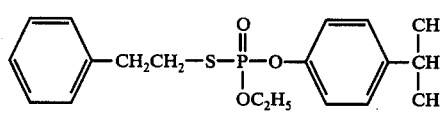 (65)
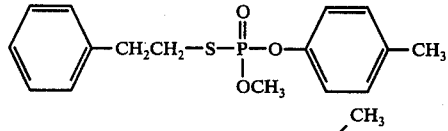 (66)
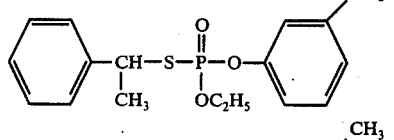 (67)
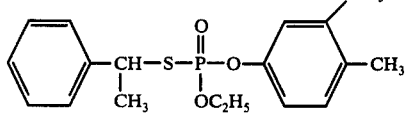 (68)

-continued
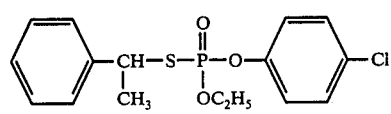 (69)
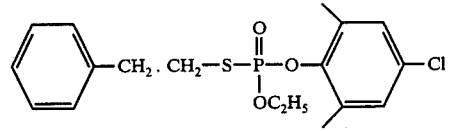 (70)
 (71)
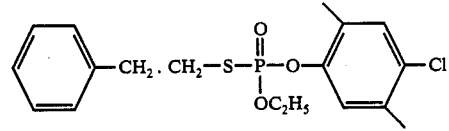 (72)
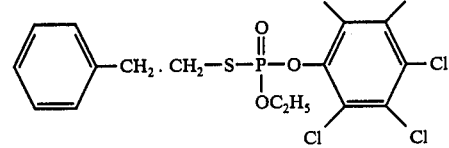 (73)
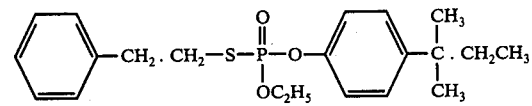 (74)
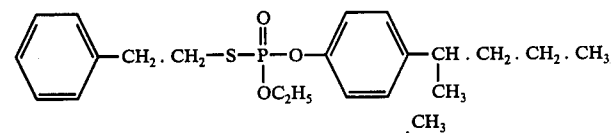 (75)
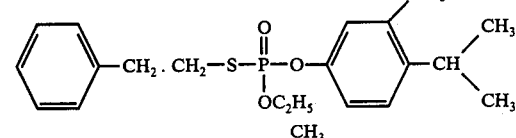 (76)
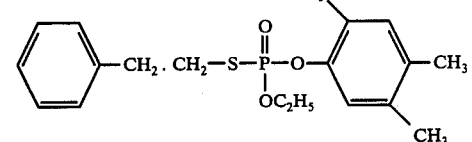 (77)
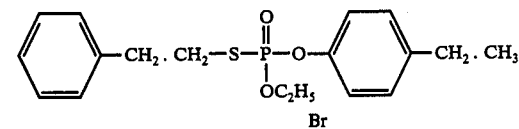 (78)
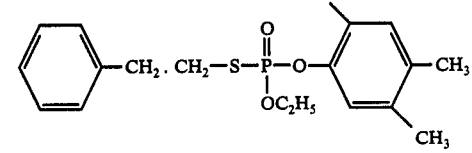 (79)
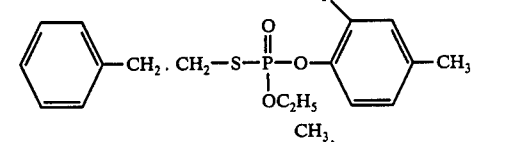 (80)

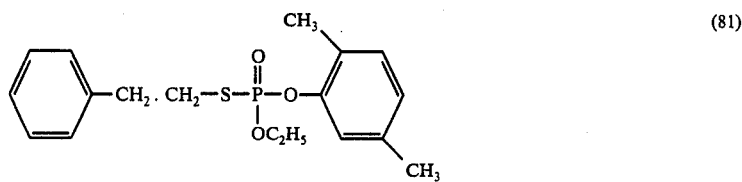
(81)
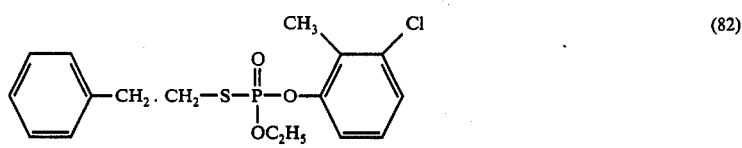
(82)
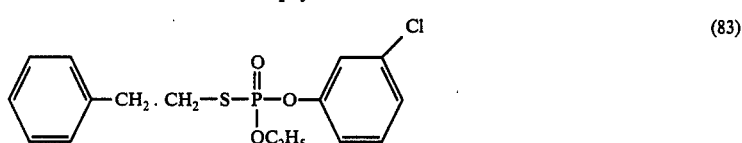
(83)
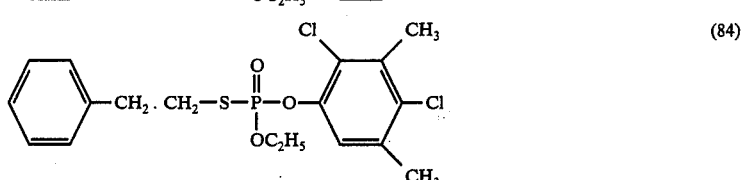
(84)
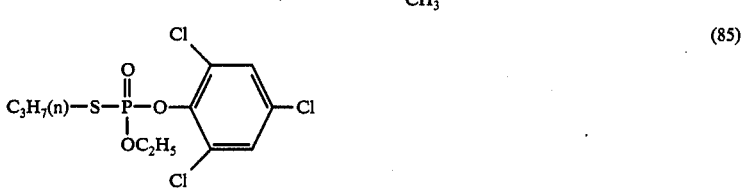
(85)
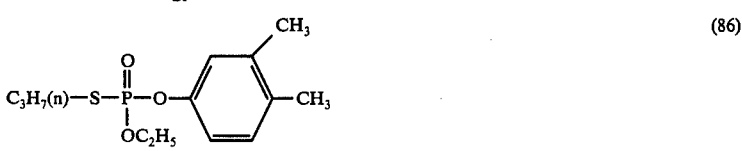
(86)
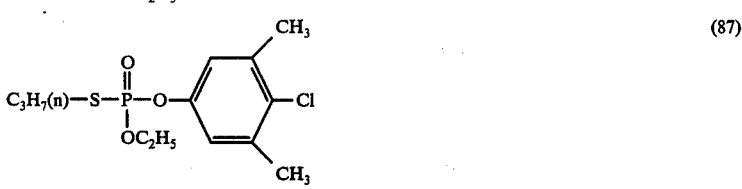
(87)
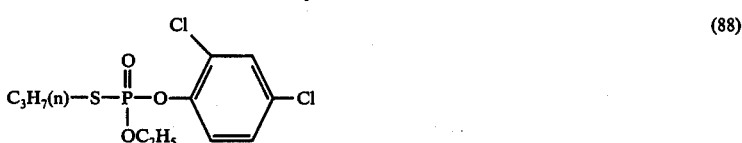
(88)
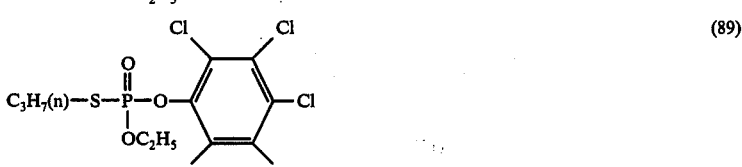
(89)
(90)
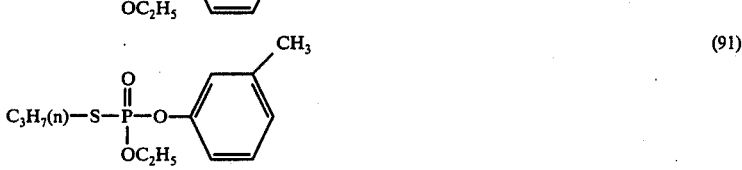
(91)

-continued
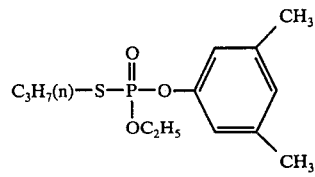 (92)
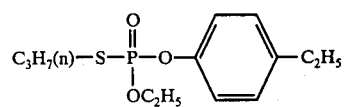 (93)
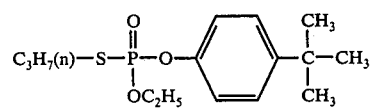 (94)
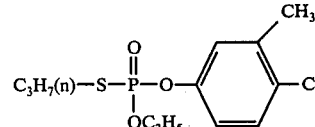 (95)
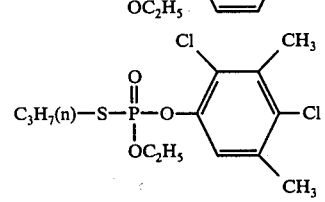 (96)
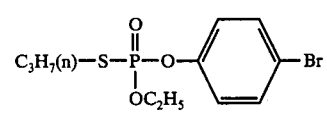 (97)
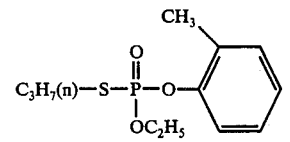 (98)
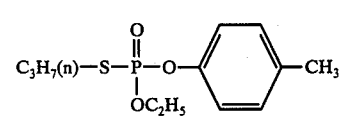 (99)
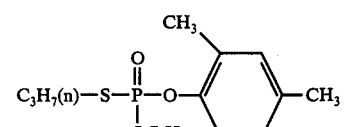 (100)
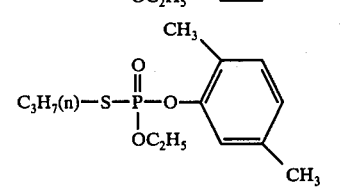 (101)
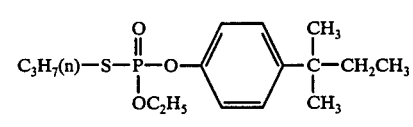 (102)
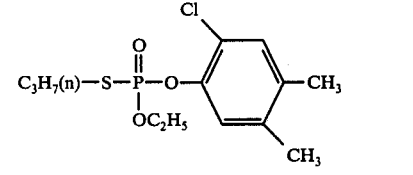 (103)

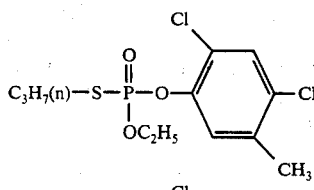 (104)

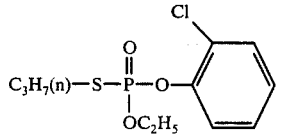 (105)

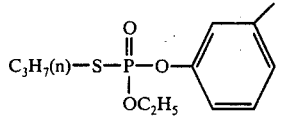 (106)

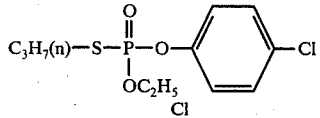 (107)

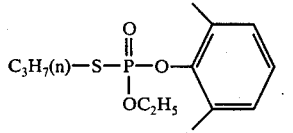 (108)

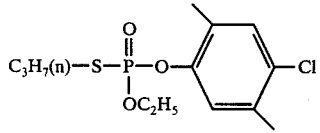 (109)

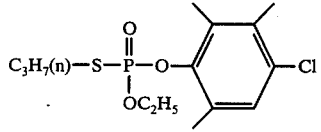 (110)

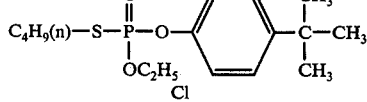 (111)

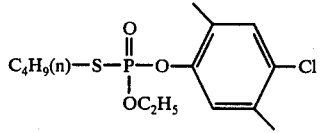 (112)

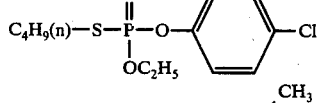 (113)

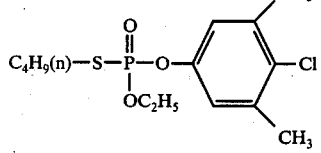 (114)

In the present invention, the thiophosphates represented by the formula [IV] and used as a starting material in the above-mentioned reaction are prepared in the following manner:

A solution of an alkali hydrosulfide represented by the formula [III] is prepared by using as a solvent a hydrated or anhydrous alcohol, alkoxyalcohol, dimethylformamide, dimethyl sulfoxide, or a mixture thereof. As the alkali hydrosulfide, there may also be used one which has been synthesized by reacting hydrogen sulfide with an alkali alcoholate or an alkali hydroxide in the above-mentioned solvent. Alternatively, a crystalline alkali hydrosulfide or an aqueous alkali hydrosulfide solution relatively high in concentration may also be used. The thus obtained alkali hydrosulfide solution is reacted with a phosphorothionate represented by the formula [II]. The reaction conditions vary depending on the kinds of starting materials and solvent employed. Generally, however, the reaction is effected at a temperature of 50° – 200° C. for a period of 30 minutes to 10 hours. After the reaction, the reaction mixture is filtered and then the solvent used and a by-produced mercaptan represented by RSH, wherein R has the same significance as mentioned previously, are removed by distillation, whereby a thiophosphate represented by the formula [IV] can be isolated as crystals. For use in the subsequent reaction with a halide of the formula [V], the thiophosphate obtained in the above manner may be employed, in general, in a liquid form without being isolated. The by-product mercaptan may be removed from the reaction mixture also during the course of the reaction.

The phosphorothionate of the formula [II], which is used as one starting material, is a known compound and is obtained according to a method disclosed in, for example, German Pat. No. 814,152.

The alkali hydrosulfide is used in an amount of 1 or more moles, preferably 1.1 – 1.2 moles, per mole of the phosphorothionate. The amount of solvent to be employed varies depending on the kind of starting material, but is ordinarily 0.5 to 5 times, preferably 1 to 3 times, the weight of the phosphorothionate.

The thiophosphates of the formula [IV], which are prepared according to the above procedures, are high in purity even at a crude state, e.g. 90% and more, and are obtained in favorable yields, e.g. 90% and more.

Several examples of the starting materials employed in practising the present invention, i.e. O,O-dialkyl-O-phenyl-phosphorothionates, hydrosulfides and halides, are raised below.

Examples of the phosphorothionate represented by the formula [II] are as follows:

O,O-Dimethyl-O-phenyl-thionophosphate.
O,O-Diethyl-O-phenyl-thionophosphate.
O,O-Dipropyl-O-phenyl-thionophosphate.
O,O-Diisopropyl-O-phenyl-thionophosphate.
O,O-Di(n)-butyl-O-phenyl-thionophosphate.
O,O-Diethyl-O-(4-bromophenyl)thionophosphate.
O,O-Diethyl-O-4-chlorophenyl-thionophospate.
O,O-Diethyl-O-3-chlorophenyl-thionophosphate.
O,O-Diethyl-O-2-chlorophenyl-thionophosphate.
O,O-Diethyl-O-2,3-dichlorophenyl-thionophosphate.
O,O-Diethyl-O-2,4-dichlorophenyl-thionophosphate.
O,O-Diethyl-O-2,5-dichlorophenyl-thionophosphate.
O,O-Diethyl-O-2,6-dichlorophenyl-thionophosphate.
O,O-Diethyl-O-2,4,6-trichlorophenyl-thionophosphate.
O,O-Diethyl-O-2,4,5-trichlorophenyl-thionophosphate.
O,O-Diethyl-O-(2,3,4,6-tetrachlorophenyl)thionophosphate.
O,O-Di(n)-propyl-O-4-chlorophenyl-thionophosphate.
O,O-Di(n)-propyl-O-2-chlorophenyl-thionophosphate.
O,O-Di(n)-butyl-O-4-chlorophenyl-thionophosphate.
O,O-Di(n)-butyl-O-2-chlorophenyl-thionophosphate.
O,O-Diethyl-O-4-methylphenyl-thionophosphate.
O,O-Diethyl-O-3-methylphenyl-thionophosphate.
O,O-Diethyl-O-2-methylphenyl-thionophosphate.
O,O-Diethyl-O-2,3-dimethylphenyl-thionophosphate.
O,O-Diethyl-O-2,4-dimethylphenyl-thionophosphate.
O,O-Diethyl-O-2,5-dimethylphenyl-thionophosphate.
O,O-Diethyl-O-2,6-dimethylphenyl-thionophosphate.
O,O-Diethyl-O-3,4-dimethylphenyl-thionophosphate.
O,O-Diethyl-O-3,5-dimethylphenyl-thionophosphate.
O,O-Diethyl-O-2,3,5-trimethylphenyl-thionophosphate.
O,O-Diethyl-O-2,4,5-trimethylphenyl-thionophosphate.
O,O-Diethyl-O-2,4,6-trimethylphenyl-thionophosphate.
O,O-Diethyl-O-2,3,5,6-tetramethylphenyl-thionophosphate.
O,O-Diethyl-O-4-ethylphenyl-thionophosphate.
O,O-Diethyl-O-3-ethylphenyl-thionophosphate.
O,O-Diethyl-O-3-(iso)-propyl-4-methylphenylthionophosphate.
O,O-Diethyl-O-2-(n)-propylphenyl-thionophosphate.
O,O-Diethyl-O-2-(iso)-propylphenyl-thionophosphate
O,O-Diethyl-O-3-(iso)-propylphenyl-thionophosphate.
O,O-Diethyl-O-4-(iso)-propylphenyl-thionophosphate.
O,O-Diethyl-O-4-(tert)-butylphenyl-thionophosphate.
O,O-Diethyl-O-2-(tert)-butylphenyl-thionophosphate.
O,O-Diethyl-O-2-(sec)-butylphenyl-thionophosphate.
O,O-Diethyl-O-3-(sec)-butylphenyl-thionophosphate.
O,O-Diethyl-O-4-(sec)-butylphenyl-thionophosphate.
O,O-Di(n)-propyl-O-4-methylbutyl-thionophosphate.
O,O-Di(n)-propyl-O-2-methylphenyl-thionophosphate.
O,O-Di(n)-butyl-O-4-methylphenyl-thionophosphate.
O,O-Diethyl-O-2,3,4,5,6-pentachlorophenyl-thionophosphate.
O,O-Diethyl-O-4-(tert)-amylphenyl-thionophosphate.
O,O-Diethyl-O-4-(sec)-amylphenyl-thionophosphate.
O,O-Diethyl-O-2-methyl-4-(iso)-propylphenyl-thionophosphate.
O,O-Diethyl-O-2-bromo-4,5-dimethylphenyl-thionophosphate.
O,O-Diethyl-O-2,4-dichloro-3,4-dimethylphenyl-thionophosphate.
O,O-Diethyl-O-3,5-dimethyl-4-chlorophenyl-thionophosphate.
O,O-Diethyl-O-3-methyl-4-chlorophenyl-thionophosphate.

Examples of the hydrosulfides are potassium and sodium hydrosulfides.

Examples of the halides are n-propyl chloride, n-propyl bromide, iso-propyl bromide, n-butyl bromide, sec-butyl bromide, chlorobromomethane, 1-chloro-2-bromoethane, 1-chloro-3-bromopropane, allyl chloride, methallyl chloride, propalgyl bbromide, 2-chloroethyl ethyl thioether, 2-chloroethyl phenyl thioether, N-chloromethyl phthalimide, 1-phenylethyl chloride, 2-phenylethyl chloride, 3-phenylpropyl bromide, 1phenylpropyl bromide, and 2-phenylpropyl bromide.

The phosphorothiolates represented by the formula [I], which are obtained in the above manner, are low in toxicity to warm-blooded animals and hence can be safely used. Moreover, they may be formulated into insecticidal and fungicidal compositions, which are high in effect of controlling injurious insects and plant diseases, and thus are markedly useful in various fields as chemicals for agriculture, horticulture, environment sanitation and stock raising.

In actual application, the compounds of the present invention may be used either independently without the incorporation of other ingredients, or in admixture with carriers, for easier use as insecticidal and fungicidal chemicals. Ordinarily, they are formulated into optional forms such as emulsifiable concentrates, wettable powders, oil sprays, dusts, ointments, granules, aerosols and fumigants, like in the case of common organic phosphorus preparations, according to procedures thoroughly known to those skilled in the art, without necessitating any special conditions. Thus, they can be put into practical uses in any desired forms by use of suitable carriers.

Further, the present compounds can be used in admixture with one or more of other chemicals to make the effects thereof broader and stronger. For example, they may be used in admixture with organophosphorus insecticides such as O,O-dimethyl-O-3-methyl-4-nitrophenyl phosphorothioate and O,O-dimethyl-S-(N-methylcarbamoyl)methyl phosphorodithioate: organochlorine preparations such as γ - 1,2,3,4,5 6-hexachlorocyclohexane and 1,1,1-trichloro-2,2-bis(p-chlorophenyl)ethane, carbamate insecticides such as 3,4-dimethylphenyl-N-methylcarbamate and 1-naphthyl-N-methylcarbamate; pyrethroid insecticides such as allethrin and phthalthrin; organochlorine fungicides such as pentachlorophenzyl alcohol and pentachlorobenzaldoxime; organosulfur fungicides; and organoarsenic fungicides. In addition, they are easily miscible with miteicides, herbicides, fertilizers, plant growth controlling agents, synergistics, attractants, repellents and the like, and hence can be formulated into multipurpose compositions, whereby synergistic effects due to mixing may be expected depending on combinations.

In order to clarify the excellent characteristics and effects of the present compounds, typical test results are shown in the following test examples, in which the figures in parentheses are the numbers of the compounds mentioned previously.

TEST EXAMPLE 1

A mottled kidney plant at the 2 leaves-stage, which had elapsed 20 days after sowing, was parasitized with a large number of carmine (*Tetranychus telarius* Linné). The leaves of said plant parasitized with the mites were individually dipped for 1 minute in each of solutions prepared by diluting with water the present compounds (1) and (2) in the form of wettable powders. Subsequently, water was given so as not to wither the leaves. After 48 hours, the alive and dead of the mites were observed. From the mortality of the mites, $LC_{50}$ values were calculated to obtain the results as set forth in Table 1.

Table 1

| Compound | $LC_{50}$ (times) |
|---|---|
| (1) | 300,000. |
| (2) | 1,000,000. |
| O,O-Dimethyl-S-(N-methylcarbamoyl)methyl phosphorodithioate | 500,000. |
| Ethyl 4,4'-dichlorobenzilate (Trade name: Akar) | 100,000. |
| 2,3-O-Dioxanedithiol S,S-bis(O,O-diethylphosphorodithioate) (Trade name: Delnav) | 1,000,000. |

TEST EXAMPLE 2

Acute Toxicity to Mice

An emulsion prepared by diluting with water the present compound (2) in the form of an emulsifiable concentrate was orally administered to male mice of about 20 g. in body-weight. From the alive and dead of the mice during 48 hours, $LD_{50}$ value was calculated to obtain the results as shown in Table 2.

Table 2

| Compound | $LD_{50}$ (mg/kg) |
|---|---|
| (2) | 181 |
| 0-Ethyl-0-p-nitrophenyl benzenephosphorothioate | 16 |
| O,O-Dimethyl-O-4-nitrophenyl phosphorothioate | 6 |

TEST EXAMPLE 3

Potted mottled kidney bean plants at the 2 leaves-stage, which had elapsed 20 days after sowing, were prarsitized with a large number of carmine mite (*Tetranychus telarius* Linné). The plants were individually dusted by use of a bell jar duster with each 4 kg/10 ares of the present compounds (2), (4) and (5) in the form of dusts. After the dusting, the plants were parasitized on different days with carmine mite (*Tetranychus telarius* Linné) and the ratios of killed mites individually from after 48 hours were investigated to obtain the results as shown in Table 3.

Table 3

| Compound | Mortality % | | | |
|---|---|---|---|---|
| | After 2 days | After 5 days | After 9 days | After 13 days |
| (2) | 100 | 100 | 99.2 | 78.6 |
| (4) | 100 | 92.4 | 81.3 | 70.3 |
| (5) | 100 | 98.8 | 83.4 | 34.4 |
| O,O-Dimethyl-S-(N-methylcarbamoyl)methyl phosphorodithioate | 100 | 100 | 79.2 | 23.4 |
| O,O-Dimethyl-o-4-nitrophenyl phosphorothioate | 100 | 100 | 51.4 | 11.2 |

TEST EXAMPLE 4

A rice plant at the tillering stage was grown in a Wagner pot. Onto the rice plant were adhered and encroached eggs of rice stem borers (*Chilo suppressalis* Walker) immediately before hatching. After 3 days, the rice plant was sprayed with 6 cc. per pot of a solution prepared by diluting with water to 2,000 times the present compound (2) in the form of a wettable powder. After allowing the rice plant to stand for an additional 3 days, the rice stem was broken and examined, and the alive and dead of the borers were observed to calculate the mortality thereof. The result was as shown in Table 4.

Table 4

| Compound | Mortality % |
|---|---|
| (2) | 95.3 |
| O,O-Dimethyl-O-3-methyl-4-nitrophenyl phosphorothioate | 94.3 |
| O,O-Dimethyl-O-4-nitrophenyl phosphorothioate | 96.0 |

TEST EXAMPLE 5

A field, in which soybean plants at the flowering stage were being parasitically damaged with a large number of carmine mites (*Tetranychus telarius* Linné), was divided into sections of each 33 m². These sections were individually sprayed with 100 1/10 ares of an emulsion prepared by diluting with water to 2,000 times the present compound (2) in the form of an emulsifiable concentrate. After 3 days, 30 soybean leaves were sampled from individual sections, and the alive and dead of the mites were observed to calculate the mortality thereof. The results are shown in Table 5.

Table 5

| Compound | Mortality (%) (average of 2 reprications) |
|---|---|
| (6) | 87.9 |
| O,O-Dimethyl-S-(N-methyl-carbamoyl)methyl phosphorodithioate | 90.0 |

TEST EXAMPLE 6

Curative Effects on Rice Blast

Rice plants (variety: WASEASAHI), which had been cultivated to the 3 leaves-stage individually in a flower pot of 9 cm. in diameter, were sprayed and inoculated with a spore suspension of rice blast fungi (*Pyricularia orysae*). After 1 day, each 7 ml. per pot of test chemical solutions at given concentrations were individually applied to the rice plants. After incubation of 3 days, the number of spots generated was counted to investigate the fungicidal effect of each test chemical, whereby the results as shown in Table 6 were obtained.

Table 6

| Compound | Active ingredient concentration (p.p.m.) | Curative value |
|---|---|---|
| (1) | 500 | 80.1 |
| (3) | 500 | 98.6 |
| (2) | 500 | 100 |
| (6) | 500 | 93.2 |
| O,O-Diethyl-S-benzyl-* phosphorothicate | 500 | 69.1 |
| Phenylmercuric acetate* | 30 | 47.6 |
| Non-treatment | — | 0 |

*Control chemicals.

In Table 6, the curative value was calculated according to the following equation:

$$\text{Curative value} = \frac{\text{Number of spots of non-treated area} - \text{Number of spots of treated area}}{\text{Number of spots of non-treated area}} \times 100.$$

TEST EXAMPLE 7

Mottled kidney bean plants at the 2 leaves-stage, which had elapsed 20 days after sowing were parasitized with a large number of carmine mites (*Tetranychus telarius* Linné). The leaves of said plants parasitised with the mites were individually dipped for 1 minute in each of solutions prepared by diluting with water the present compounds (10), (11), (13), (14) and (15) in the form of wettable powders. Subsequently, water was added so as not to wither the leaves. After 48 hours, the alive and dead of the mites were observed. From the mortality of the mites, $LC_{50}$ values were calculated to obtain results as shown in Table 7.

Table 7

| Compound | $LC_{50}$ (diluted times) |
|---|---|
| (10) | 6,000,000 |
| (11) | 256,000 |
| (13) | 1,000,000 |
| (14) | 3,000,000 |
| (15) | 4,000,000 |
| O,O-Dimethyl-S-(N-methyl-* carbamoyl)methyl phosphorodithioate | 500,000 |
| Ethyl-4,4'-dichlorobenzilate* | 100,000 |
| 2,3-p-Dioxane S,S-bis-(O,O-* diethyl phosphorodithioate) | 1,000,000 |

*Control chemicals

TEST EXAMPLE 8

Dipping effects on Adzuki Bean Weevils

Adzuki bean weevils (*Callosobruchus chinensis* Linné) within one day after emergence were dipped for 1 minute in each of emulsions prepared by diluting with water the present compounds (9) to (12), and (14) to (16) in the form of emulsifiable concentrates. Excess liquid on the surfaces of the weevil was removed on a filter paper. After 24 hours, the alive and dead of the weevils were observed, and $LC_{50}$ values were calculated to obtain the results as shown in Table 8.

Table 8

| Compound | $LC_{50}$ (diluted times) |
|---|---|
| (9) | 200,000 |
| (10) | 300,000 |
| (11) | 105,000 |
| (12) | 180,000 |
| (14) | 115,000 |
| (15) | 210,000 |
| (16) | 350,000 |
| O,O-Dimethyl-O-3-methyl-4-nitrophenyl phosphorothioate | 55,000 |
| O,O-Dimethyl-S-(1,2-dicarboethoxyethyl) phosphorodithioate | 8,800 |
| O-Ethyl-O-p-nitrophenyl phenylphosphonothiorate | 10,000 |

TEST EXAMPLE 9

Acute Toxicity to Mice

Emulsions prepared by diluting with water the present compounds (14), (18), (20), (22), (85), (89), (97), (104), (109), (110) and (114) in the form off emulsifiable concentrates were orally administered individually to male mice of about 20 g. in body weight. From the alive and dead of the mice after 48 hours, $LD_{50}$ values were calculated according to Richfield Method to obtain the results as shown in Table 9.

Table 9

| Compound | $LD_{50}$ (mg/kg) |
|---|---|
| (14) | 80 |
| (18) | 100 |
| (20) | 121 |
| (22) | 500 |
| (85) | 200 |
| (89) | 300 |
| (97) | 200 |
| (104) | 200 |
| (109) | 300 |
| (110) | 300 |
| (114) | 100 |
| O-Ethyl-O-p-nitrophenyl phenylphosphonothiorate | 16 |
| O,O-Dimethyl-O-4-nitrophenyl phosphorothioate | 5 |

TEST EXAMPLE 10

Potted mottled kidney bean plants at the 2 leaves-stage, which had elapsed 20 days after sowing, were parasitized with a large number of carmine mite (*Tet-* ranychus teralius Linné). The plants were individually dusted by use of a bell jar duster with each 4 kg/10 ares of the present compounds (9), (13), (23), (24) and (30) in the form of dusts. After the dusting, the plants were parasitized on different days with the mites, and the ratios of killed mites individually from after 48 hours were investigated to obtain the results as shown in Table 10.

Table 10

| Compound | Mortality (%) | | | |
|---|---|---|---|---|
| | After 2 days | After 5 days | After 9 days | After 13 days |
| (9) | 100 | 99.2 | 83.4 | 53.4 |
| (13) | 100 | 95.3 | 92.1 | 61.2 |
| (23) | 100 | 92.4 | 81.3 | 70.3 |
| (24) | 100 | 93.8 | 79.2 | 61.2 |
| (30) | 100 | 92.4 | 76.0 | 38.4 |
| O,O-Dimethyl-S-(N-methylcarbamoyl)methyl phosphorodithioate | 100 | 100 | 79.2 | 23.4 |
| O,O-Dimethyl-O-4-nitrophenyl phosphorothioate | 100 | 100 | 51.4 | 11.2 |

TEST EXAMPLE 11

Rice plants at the tillering stage were individually grown in Wagner pots. Onto the rice plants were adhered and encroached eggs of rice steam borers (*Chilo suppressalis* Walker) immediately before hatching. After 3 days, the rice plants were individually sprayed with each 6 cc. per pot of solutions prepared by diluting with water to 2,000 times the present compounds (11), (14), (15) and (31) in the form of wettable powders. After allowing the rice plants to stand for additional 3 days, the rice stems were broken and examined, and the alive and dead of the borers were observed to calculate the mortality thereof. The results were as shown in Table 11.

Table 11

| Compound | Mortality (%) |
|---|---|
| (11) | 96.3 |
| (14) | 93.4 |
| (15) | 98.2 |
| (31) | 99.2 |
| O,O-Dimethyl-O-3-methyl-4-nitrophenyl phosphorothioate | 94.3 |
| O,O-Dimethyl-O-4-nitrophenyl phosphorothioate | 96.0 |

TEST EXAMPLE 12

Well water was charged into a 500 cc. beaker. Into the water, full grown larvae of northern house mosquitoes (*Culex pipiens pallens* Coquillett) were liberated, and the present compounds (12), (16), (17), (23), (25), (26), (27), (29), (30), (85), (87), (88), (89), (94), (95), (96), (97), (100), (102), (103), (104), (105), (106), (107), (108), (109) and (110) in the form of granules were individually charged. After 24 hours, the alive and dead of the mosquito larvae were observed and, from the mortality thereof, $LC_{50}$ values were calculated to obtain the results as shown in Table 12.

Table 12

| Compound | $LC_{50}$ (p.p.m.) |
|---|---|
| (12) | 0.02 |
| (16) | 0.03 |
| (17) | 0.09 |
| (23) | 0.009 |
| (25) | 0.003 |
| (26) | 0.01 |
| (27) | 0.03 |

Table 12-continued

| Compound | $LC_{50}$ (p.p.m.) |
|---|---|
| (29) | 0.022 |
| (30) | 0.089 |
| (85) | 0.01 |
| (87) | 0.054 |
| (88) | 0.01 |
| (89) | 0.00135 |
| (94) | 0.07 |
| (95) | 0.021 |
| (96) | 0.0078 |
| (97) | 0.022 |
| (100) | 0.096 |
| (102) | 0.064 |
| (103) | 0.034 |
| (104) | 0.0054 |
| (105) | 0.034 |
| (106) | 0.022 |
| (107) | 0.048 |
| (108) | 0.022 |
| (109) | 0.017 |
| (110) | 0.01 |

TEST EXAMPLE 13

A field, in which soybean plants at the flowering stage were being parasitically damaged with a large number of carmine mites (*Tetravenus terarius* Linné), was divided into blocks of each 33 m². These blocks were individually sprayed with each 100 Kg/10 ares of emulsions prepared by diluting with water to 2,000 times the present compounds (12), (16), (17), (21), (23), (25), (26), (27), (28), (32), (33), (34), (85), (87), (88), (92), (94), (95), (97), (105), (109) and (114) in the form of emulsifiable concentrates. After 3 days, 30 soybean leaves were sampled from individual sections, and the alive and dead of the mites were observed to calculate the mortality thereof. The results are shown in Table 13.

Table 13

| Compound | Mortality (%) (average of 2 sections) |
|---|---|
| (12) | 100.0 |
| (16) | 100.0 |
| (17) | 100.0 |
| (21) | 92.3 |
| (23) | 95.2 |
| (25) | 99.7 |
| (26) | 87.0 |
| (27) | 100.0 |
| (28) | 98.2 |
| (32) | 92.4 |
| (33) | 90.7 |
| (34) | 96.4 |
| (85) | 100.0 |
| (87) | 90.6 |
| (88) | 93.3 |
| (92) | 87.6 |
| (94) | 85.1 |
| (95) | 91.7 |
| (97) | 94.8 |
| (105) | 90.5 |
| (109) | 91.1 |
| (114) | 92.2 |
| O,O-Dimethyl-S-(N-methylcarbamoyl)methyl phosphorodithioate | 90.0 |

TEST EXAMPLE 14

Curative effect on rice blast

Rice plants (variety: WASEASAHI), which had been cultivated to the 3 leaves-stage individually in flower pots of 9 cm. in diameter, were sprayed and inoculated with a spore suspension of rice blast fungi (*Pyricularia oryzae*). After one day, each 7 ml. per pot of test chemical solutions at given concentrations were individually applied to the rice plants. After incubation of 4 days, the number of spots generated was counted to investigate the fungicidal effect of each test chemical, whereby the results as shown in Table 14 were obtained.

Table 14

| Compound | Active ingredient concentration (p.p.m.) | Curative Value |
|---|---|---|
| (11) | 1,000 | 87.1 |
| (14) | 1,000 | 86.4 |
| (19) | 1,000 | 89.3 |
| (23) | 1,000 | 99.5 |
| (24) | 1,000 | 90.8 |
| (25) | 1,000 | 92.7 |
| (26) | 1,000 | 89.5 |
| (34) | 1,000 | 97.2 |
| (85) | 1,000 | 98.6 |
| (88) | 1,000 | 87.1 |
| (89) | 1,000 | 100 |
| (96) | 1,000 | 69.2 |
| (97) | 1,000 | 71.3 |
| (108) | 1,000 | 58.7 |
| (109) | 1,000 | 89.5 |
| (110) | 1,000 | 89.3 |
| (112) | 1,000 | 91.8 |
| (113) | 1,000 | 63.6 |
| (114) | 1,000 | 70.7 |
| Control: 0,0-Diethyl-S-benzyl-phosphorothioate (trade name: Kitazin) | 1,000 | 78.6 |
| Control: Phenylmercuric acetate | 30 | 47.7 |
| Non-treatment | 0 | 0 |

The curative value was calculated according to the equation shown in Test Example 6.

TEST EXAMPLE 15

Insecticidal effects of Small brown plant hopper (*Laoclelphex striatellus* Fallén)

Rice seedlings (15–20 cm. in height), which had elapsed 15 days after germination, were individually dipped for 1 minute in emulsions prepared by diluting with water to given concentrations the present compounds (10), (14), (19), (23), (32), (85), (88), (90), (93), (94), (103), (104), (106) and (109) in the form of emulsifiable concentrates.

After air-drying, the rice seedlings were individually charged into test glass tubes, and 20–30 plant hoppers (*Laodelphax striatellus* Fallén) were liberated in each tube, and the tube was covered with gauze. After 24 hours, the alive and dead of the plant hoppers were observed to calculate the mortality thereof. From the mortality, $LC_{50}$ values were calculated to obtain the results as shown in Table 15.

Table 15

| Compound | $LC_{50}$ (times diluted) |
|---|---|
| (10) | 512,000 |
| (14) | 128,000 |
| (19) | 32,000 |
| (23) | 48,000 |
| (29) | 240,000 |
| (31) | 50,000 |
| (85) | 100,000 |
| (88) | 250,000 |
| (90) | 150,000 |
| (93) | 64,000 |
| (94) | 80,000 |
| (103) | 64,000 |
| (104) | 150,000 |
| (106) | 64,000 |
| (109) | 70,000 |

TEST EXAMPLE 16

Mottled kidney bean plants at the 2 leaves-stage, which had elapsed 20 days after sowing, were parasitized with a large number of carmine mites (*Tetranychus terarius* Linné). The leaves of said plants parasitized with the mites were individually dipped for 1 minute in each of solutions prepared by diluting with water the present compounds (35) to (37), (41) to (44) and (46) to (56) in the form of wettable powders. Subsequently, water was added so as not to wither the leaves. After 48 hours, the alive and dead of the mites were observed. From the mortality of the mites, $LC_{50}$ values were calculated to obtain the results as shown in Table 16.

Table 16

| Compound | $LC_{50}$ (times diluted) |
|---|---|
| (35) | 12,000,000 |
| (36) | 540,000 |
| (37) | 50,000 |
| (41) | 1,100,000 |
| (42) | 1,100,000 |
| (43) | 11,000 |
| (44) | 330,000 |
| (46) | 80,000 |
| (47) | 15,000 |
| (48) | 150,000 |
| (49) | 60,000 |
| (50) | 90,000 |
| (51) | 1,200,000 |
| (52) | 900,000 |
| (53) | 1,000,000 |
| (54) | 70,000 |
| (55) | 90,000 |
| (56) | 83,000 |

TEST EXAMPLE 17

Mottled kidney bean plants at the 2 leaves-stage, which has elapsed 20 days after sowing, were parasitized with a large number of carmine mites (*Tetranychus telarius* Linné). The leaves of said plants paracitized with the mites were individually dipped for 1 minute in each of solutions prepared by diluting with water the present compounds (58) to (62), (64), (67) and (69) in the form of wettable powders. Subsequently, water ws added so as not to wither the leaves. After 48 hours, the alive and dead of the mites were observed. From the mortality of the mites, $LC_{50}$ values were calculated to obtain the results shown in Table 17.

Table 17

| Compound | $LC_{50}$ (times) |
|---|---|
| (58) | 4,000,000 |
| (59) | 1,250,000 |
| (60) | 460,000 |
| (61) | 340,000 |
| (62) | 100,000 |
| (64) | 2,000,000 |
| (67) | 1,000,000 |
| (69) | 350,000 |
| 0,0-Dimethyl-S-(N-methyl-carbamoyl)methyl phosphorodithioate | 500,000 |
| Ethyl 4,4'-dichlorobenzilate | 100,000 |
| 2,3-p-Dioxane S,S-bis-(0,0-diethyl phosphorodithioate) | 1,000,000 |

TEST EXAMPLE 18

Dipping effects on Adzuki bean weevils

Adzuki been weevils (*Callosobruchus chinensis* Linné) within 1 day after emergence were dipped for 1 minute in each of emulsions prepared by diluting with water the present compounds (58), (60), (61), (85) – (89), (93) – (97), (101), (103), (104), (106), (109), (110) and (113) in the form of emulsifiable concentrates. Excess liquid on the surfaces of the weevils was removed on a filter paper.

After 24 hours, the alive and dead of the weevils were observed, and $LC_{50}$ values were calculated to obtain the results as shown in Table 18.

Table 18

| Compound | $LC_{50}$ (times) |
|---|---|
| (58) | 108,000 |
| (60) | 108,000 |
| (61) | 135,000 |
| (85) | 410,000 |
| (86) | 120,000 |
| (87) | 270,000 |
| (88) | 490,000 |
| (89) | 600,000 |
| (93) | 200,000 |
| (94) | 500,000 |
| (95) | 220,000 |
| (96) | 340,000 |
| (97) | 245,000 |
| (101) | 122,000 |
| (103) | 350,000 |
| (104) | 460,000 |
| (106) | 140,000 |
| (109) | 330,000 |
| (110) | 420,000 |
| (113) | 228,000 |
| 0,0-Dimethyl-0-3-methyl-4-nitrophenyl phosphorothioate | 55,000 |
| 0,0-Dimethyl-S-(1,2-dicarboethoxy)ethyl phosphorodithicate | 8,800 |
| 0-Ethyl-0-p-nitrophenyl phenylphosphonothiorate | 10,000 |

TEXT EXAMPLE 19

Potted mottled kidney bean plants at the 2 leaves-stage, which had elapsed 20 days after sowing, were parasitized with a large number of carmine mites (*Tetranychus telarius* Linné). The plants were individually dusted by use of a bell jar duster with each 4 kg/10 ares of the present compounds (58) to (66), (62), (64) to (66), (85), (87), (88), (92), (94), (95), (97), (105), (109), (113) and (114) in the form of dusts. After the dusting, the plants were parasitized on different days with the mites, and the ratios of killed mites individually from after 48 hours were investigated to obtain the results as shown in Table 19.

Table 19

| Compound | Mortality (%) After 2 days | After 5 days | After 9 days | After 13 days |
|---|---|---|---|---|
| (58) | 100 | 100 | 100 | 77.4 |
| (59) | 100 | 100 | 100 | 83.2 |
| (60) | 100 | 100 | 100 | 91.4 |
| (61) | 100 | 100 | 99.4 | 77.8 |
| (62) | 100 | 100 | 100 | 76.4 |
| (63) | 100 | 100 | 91.3 | 71.9 |
| (64) | 100 | 100 | 98.2 | 83.4 |
| (65) | 100 | 100 | 99.5 | 91.2 |
| (66) | 100 | 100 | 100 | 90.4 |
| (85) | 100 | 100 | 100 | 70.5 |
| (87) | 100 | 93.7 | 82.3 | 31.6 |
| (88) | 100 | 100 | 91.1 | 52.1 |
| (92) | 100 | 83.4 | 67.8 | 20.9 |
| (94) | 100 | 87.5 | 70.9 | 18.7 |
| (95) | 100 | 91.3 | 80.7 | 35.3 |
| (97) | 100 | 100 | 94.2 | 68.6 |
| (105) | 100 | 95.6 | 85.4 | 41.5 |
| (109) | 100 | 96.1 | 85.7 | 40.5 |
| (113) | 100 | 91.9 | 78.4 | 21.1 |
| (114) | 100 | 100 | 92.6 | 53.3 |
| 0,0-Dimethyl-S-(N-methylcarbamoyl)methyl phosphorodithioate | 100 | 100 | 79.2 | 23.4 |
| 0,0-Dimethyl-0-4-nitrophenyl phosphorothioate | 100 | 100 | 51.4 | 11.2 |

TEST EXAMPLE 20

Rice plants at the tillering stage were individually grown in Wagner pots. Onto the rice plants were ad- hered and encroached eggs of rice stem borers (*Chilo suppressalis* Walker) immediately before hatching. After 3 days, the rice plants were individually sprayed with each 6 cc. per pot of solutions prepared by diluting with water to 2,000 times the present compounds (58) to (62), (65), (68), (85), (88), (96), (104), (107), (109), (110) and (112) in the form of wettable powders. After allowing the rice plants to stand for additional 5 days, the rice stems were broken and examined, and the alive and dead of the borers were observed to calculate the mortality thereof. The results were as shown in Table 20.

Table 20

| Compound | Mortality (%) |
|---|---|
| (58) | 81.4 |
| (59) | 95.3 |
| (60) | 91.8 |
| (61) | 92.6 |
| (62) | 94.4 |
| (65) | 91.4 |
| (68) | 96.7 |
| (85) | 98.1 |
| (88) | 94.4 |
| (96) | 89.6 |
| (104) | 90.5 |
| (107) | 97.0 |
| (109) | 96.3 |
| (110) | 94.5 |
| (112) | 93.7 |
| 0,0-Dimethyl-0-3-methyl-4-nitrophenyl phosphorothioate | 94.3 |
| 0,0-Dimethyl-0-4-nitrophenyl phosphorothiate | 96.0 |

TEST EXAMPLE 21

Mottled kidney bean plants at the 2 leaves-stage, which had elapsed 20 days after sowing, were parasitized with a large number of carmine mites (*Tetranvchus telarius* Linné). The leaves of said plants parasitized with the mites were individually dipped for 1 minute in each of solutions prepared by diluting with water the present compounds (29) and (70) to (114) in the form of wettable powders. Subsequently, water was added so as not to wither the leaves. After 48 hours, the alive and dead of the mites were observed. From the mortality of the mites, $LC_{50}$ values were calculated to obtain the results as shown in Table 21.

Table 21

| Compound | $LC_{50}$ (times) |
|---|---|
| (29) | 400,000 |
| (70) | 200,000 |
| (71) | 210,000 |
| (72) | 340,000 |
| (73) | 180,000 |
| (74) | 44,000 |
| (75) | 250,000 |
| (76) | 94,000 |
| (77) | 220,000 |
| (78) | 50,000 |
| (79) | 60,000 |
| (80) | 150,000 |
| (81) | 40,000 |
| (82) | 20,000 |
| (83) | 70,000 |
| (84) | 180,000 |
| (85) | 17,000,000 |
| (86) | 450,000 |
| (87) | 2,000,000 |
| (88) | 3,000,000 |
| (89) | 6,000,000 |
| (90) | 1,000,000 |
| (91) | 480,000 |
| (92) | 660,000 |
| (93) | 400,000 |
| (94) | 6,600,000 |
| (95) | 8,500,000 |
| (96) | 9,000,000 |
| (97) | 35,000,000 |
| (98) | 170,000 |
| (99) | 250,000 |

Table 21-continued

| Compound | LC$_{50}$ (times) |
|---|---|
| (100) | 440,000 |
| (101) | 1,600,000 |
| (102) | 1,200,000 |
| (103) | 3,000,000 |
| (104) | 14,000,000 |
| (105) | 1,024,000 |
| (106) | 4,000,000 |
| (107) | 3,000,000 |
| (108) | 7,000,000 |
| (109) | 2,500,000 |
| (110) | 8,000,000 |
| (111) | 900,000 |
| (112) | 4,500,000 |
| (113) | 800,000 |
| (114) | 2,048,000 |

The present invention is illustrated below with reference to examples, but it is needless to say that the examples are merely illustrative and the present invention is by no means limited only to these examples.

EXAMPLE 1

6.7 g. (0.12 mole) of potassium hydroxide was dissolved in 50 ml. of ethyl alcohol. The solution was saturated with hydrogen sulfide to form an ethyl alcohol solution of potassium hydrosulfide. To this solution, 29.6 g. (0.12 mole) of O,O-diethyl-O-phenylthionophosphate was added, and the mixture was refluxed with stirring for 4 hours. After cooling to room temperature, the mixture was charged with 16.4 g. (0.12 mole) of n-butyl bromide, and was then refluxed with stirring for 5 hours. After removing the solvent by distillation, the residue was charged with toluene, was washed with 5% sodium carbonate and was then washed several times with water, and the toluene layer was dried with anhydrous sodium sulfate. Subsequently, toluene was removed by reduced pressure distillation to obtain 27.0 g. of a pale yellow, oily O-ethyl-O-phenyl-S-n-butyl phosphorothiolate, $n_D^{20}$ 1.5125; yield 82.1%.

Elemental analysis for $C_{12}H_{19}O_3PS$:

| | Calculated | Found |
|---|---|---|
| P (%) | 11.29 | 11.43 |
| S (%) | 11.69 | 11.97 |

EXAMPLE 2

6.7 g. (0.12 mole) of potassium hydroxide was dissolved in 50 ml. of ethyl alcohol. The solution was saturated with hydrogen sulfide to form an ethyl alcohol solution of potassium hydrosulfide. To this solution, 29.6 g. (0.12 mole) of O,O-diethyl-O-phenyl-thionophosphate was added, and the mixture was refluxed with stirring for 4 hours. After removing ethyl alcohol by reduced pressure distillation, the deposited crystals were suspended in ether, filtered and dried to obtain 28.0 g. of white crystals, yield 91.0%, m.p. 140° C.

25.6 g. (0.1 mole) of the thus obtained thiophosphate was dissolved in 100 ml. of ethyl alcohol. To this solution, 14.3 g. (0.1 mole) of 1-chloro-2-bromoethane was added at room temperature, and the mixture was refluxed with stirring for 7 hours.

Thereafter, the reaction mixture was treated in the same manner as in Example 1 to obtain 20.0 g. of a pale yellow, oily O-ethyl-O-phenyl-S-2-chloroethyl-phosphorothiolate, $n_D^{18}$ 1.5324; yield 71.2%.

| | Calculated | Found |
|---|---|---|
| P (%) | 11.03 | 11.24 |
| S (%) | 11.42 | 11.71 |
| Cl (%) | 12.63 | 12.51 |

EXAMPLE 3

25.6 g. (0.1 mole) of a potassium salt of O-ethyl-O-phenylphosphorothioate, which had been prepared in the same manner as in Example 2, was dissolved in 100 ml. of ethyl alcohol. To the solution, 12.1 g. (0.1 mole) of allyl bromide was added at room temperature, and the mixture was stirred at 60° -70° C. for 3 hours. Thereafter, the mixture was treated in the same manner as in Example 1 to obtain 25.1 g. of a pale yellow oily O-ethyl-O-phenyl-S-allylphosphorothiolate, $n_D^{20}$ 1.5310; yield 97.3%.

Elementary analysis for $C_{11}H_{15}O_3PS$:

| | Calculated | Found |
|---|---|---|
| P (%) | 11.99 | 11.87 |
| S (%) | 12.41 | 12.68 |

EXAMPLE 4

24.0 g. (0.1 mole) of a sodium salt of O-ethyl-O-phenylphosphorothioate, which had been prepared in the same manner as in Example 2, was dissolved in 100 ml. of ethyl alcohol. To the solution, 18.5 g. (0.1 mole) of 2-phenylethyl bromide was added at room temperature. Further, a catalytic amount of potassium iodide was added thereto. Subsequently, the mixture was refluxed with stirring for 5 hours and was then treated in the same manner as in Example 1 to obtain 29.2 g. of a pale yellow, oily O-ethyl-O-phenyl-S-2-phenylethyl-phosphorothiolate, $n_D^{22}$ 1.5567; yield 90.6%

Elementary analysis for $C_{16}H_{19}O_3PS$:

| | Calculated | Found |
|---|---|---|
| P (%) | 9.61 | 9.60 |
| S (%) | 9.95 | 10.21. |

EXAMPLE 5

25.6 g. (0.1 mole) of a potassium salt of O-ethyl-O-phenyl-phosphorothioate, which had been prepared in the same manner as in Example 2, ws dissolved in 100 ml. of ethyl alcohol. To the solution, 17.3 g. (0.1 mole) of 2-phenylthioethyl chloride was added at room temperature. Further, a catalytic amount of potassium iodide was added thereto. Subsequently, the mixture was refluxed with stirring for 5 hours and was then treated in the same manner as in Example 1 to obtain 33.1 g. of a pale yellow, oily O-ethyl-O-phenyl-S-2-phenylthioethyl-phosphorothiolate, $n_D^{23}$ 1.5790; yield 93.3%.

Elementary analysis for $C_{10}H_{19}O_3PS_2$:

| | Calculated | Found |
|---|---|---|
| P (%) | 8.74 | 8.49 |
| S (%) | 18.09 | 18.22. |

EXAMPLE 6

25.6 g. (0.1 mole) of O-ethyl-O-phenylphosphorothioate, which had been prepared in the same manner as in Example 2, was dissolved in 100 ml. of ethyl alcohol. To the solution, 19.6 g. (0.1 mole) of N-chloromethylphthalimide was added at room temperature. Further, a catalytic amount of potassium iodide was added thereto. Subsequently, the mixture was refluxed with stirring for 3 hours and was then treated in the same manner as in Example 1 to obtain 37.1 g. of a colorless, oily O-ethyl-O-phenyl-S-phthalimide methyl phosphorothiolate, $n_D^{21}$ 1.5850 yield 98.2%.

Elementary analysis for $C_{17}H_{16}NO_5PS$:

|       | Calculated | Found |
|-------|-----------|-------|
| P (%) | 8.21      | 8.44  |
| S (%) | 8.50      | 8.73  |
| N (%) | 3.71      | 3.66  |

EXAMPLE 7

6.7 g. (0.12 mole) of potassium hydroxide was dissolved in 50 ml. of ethyl alcohol. The solution was saturated with hydrogen sulfide to form an ethyl alcohol solution of potassium hydrosulfide. To this solution 31.2 g. (0.12 mole) of O,O-diethyl-O-4-methylphenyl-thionophosphate was added, and the mixture was refluxed with stirring for 5 hours. After cooling to room temperature, the mixture was charged with 22.2 g. (0.12 mole) of 2-phenylethyl bromide and further with a catalytic amount of potassium iodide. Subsequently, the mixture was refluxed with stirring for 5 hours. After removing the solvent from the reaction mixture by distillation, the residue was charged with toluene, was washed with 5% sodium carbonate and was then washed several times with water, and the toluene layer was dried with anhydrous sodium sulfate. Subsequently, toluene was removed by reduced pressure distillation to obtain 34.4 g. of a pale yellow, oily O-ethyl-O-4-methylphenyl-S-2-phenylethylphosphorothiolate, $n_{D25}$ 1.5536; yield 85.2 %.

Elementary analysis for $C_{17}H_{21}O_3PS$:

|       | Calculated | Found |
|-------|-----------|-------|
| P (%) | 9.21      | 9.18  |
| S (%) | 9.53      | 9.74  |

EXAMPLE 8

6.7 g. (0.12 mole) of potassium hydroxide was dissolved in 50 ml. of ethyl alcohol. The solution was saturated with hydrogen sulfide to form an ethyl alcohol solution of potassium hydrosulfide. To this solution, 36.2 g. (0.12 mole) of O,O-diethyl-O-4-(tert)butyl-phenylthionophosphate was added and the mixture was refluxed with stirring for 6 hours. After cooling to room temperature, the mixture was charged with 22.2 g. (0.12 mole) of 2-phenylethyl bromide and a catalytic amount of potassium iodide, and was then refluxed with stirring for 7 hours. Subsequently, the mixture was treated in the same manner as in Example 1 to obtain 37.6 g. of a pale yellow, oily O-ethyl-O-4-(tert)-butylhenyl-S-2-phenylethyl phosphorothiolate, $n_D^{29}$ 1.5412; yield 82.7%.

Elementary analysis for $C_{20}H_{27}O_3PS$:

|       | Calculated | Found |
|-------|-----------|-------|
| P (%) | 8.18      | 8.18  |
| S (%) | 8.47      | 8.57  |

EXAMPLE 9

28.4 g. (0.1 mole) of a potassium salt of O-ethyl-O-3,4-dimethylphenyl phosphorothioate, which had been prepared in the same manner as in Example 1, was dissolved in 100 ml. of water. To the solution, 18.5 g. (0.1 mole) of 2-phenylethyl bromide and a catalytic amount of potassium iodide was added, and the mixture was stirred at 80° C. for 5 hours. Subsequently, the reaction mixture was treated in the same manner as in Example 1 to obtain 31.3 g. of a brown, oily O-ethyl-O-3,4-dimethylphenyl-S-2-phenylethyl-phosphorothiolate, $n_D^{28}$ 1.5530; yield 89.2%.

Elementary analysis for $C_{18}H_{23}O_3PS$:

|       | Calculated | Found |
|-------|-----------|-------|
| P (%) | 8.84      | 8.67  |
| S (%) | 9.15      | 9.18  |

EXAMPLE 10

6.7 g. (0.12 mole) of potassium hydroxide was dissolved in 50 ml. of ethyl alcohol. The solution was saturated with hydrogen sulfide to form an ethyl alcohol solution of potassium hydrogen sulfide. To this solution, 31.2 g. (0.12 mole) of O,O-diethyl-O-3-methylphenylthionophosphate was added, and the mixture was refluxed with stirring for 6 hours. After cooling to room temperature, the mixture was charged with 22.2 g. (0.12 mole) of 2-phenylethyl bromide and was then refluxed with stirring for 5 hours. Subsequently, the reaction mixture was treated in the same manner as in Example 1 to obtain 32.8 g. of a pale yellow, oily O-ethyl-O-3-methylphenyl-S-2-phenylethyl phosphorothiolate, $n_D^{25}$ 1.5522; yield 81.3%.

Elementary analysis for $C_{17}H_{21}O_3PS$:

|       | Calculated | Found |
|-------|-----------|-------|
| P (%) | 9.21      | 9.22  |
| S (%) | 9.53      | 9.71  |

EXAMPLE 11

6.7 g. (0.12 mole) of potassium hydroxide was dissolved in 50 ml. of ethyl alcohol. The solution was saturated with hydrogen sulfide to form an ethyl alcohol solution of potassium hydroxide. To this solution, 33.7 g. (0.12 mole) of O,O-diethyl-O-4-chlorophenyl-thionophosphate was added, and the mixture was refluxed with stirring for 4 hours. After removing ethyl alcohol by reduced pressure distillation, deposited crystals were suspended in ether, filtered and dried to obtain 32.2 g. of white crystals, yield 92.3%; m.p. 154° – 156° C.

29.1 g. (0.1 mole) of the thus obtained thiophosphate was dissolved in 100 ml. of water. To the solution, 18.5 g. (0.1 mole) of 2-phenylethyl bromide was added at room temperature, and the mixture was stirred at 80° C. for 5 hours. Subsequently, the reaction mixture was treated in the same manner as in Example 1 to obtain 33.5 g. of a pale yellow, oily O-ethyl-O-4-chlorophenyl-S-2-phenylethyl phosphorothiolate, $n_D^{26}$ 1.5610; yield 94.0%.

Elementary analysis for $C_{16}H_{18}ClO_3PS$:

|  | Calculated | Found |
|---|---|---|
| P (%) | 8.68 | 8.48 |
| S (%) | 8.99 | 8.90 |
| Cl (%) | 9.94 | 10.14 |

EXAMPLE 12

A mixture comprising 30.5 g. of a potassium salt of O-ethyl-O-3-methyl-4-chlorophenyl-phosphorothioate, which had been prepared in the same manner as in Example 1, 100 ml. of ethanol and 18.5 g. of 2-phenylethyl bromide was refluxed for 5 hours and was then subjected to ordinary after-treatments to obtain a pale yellow, oily O-ethyl-O--3-methyl-4-chlorophenyl-S-2-phenylethyl-phosphorothiolate, $n_D^{31}$ 1.5568; yield 93%.

Elementary analysis for $C_{17}H_{20}ClO_3PS$:

|  | Calculated | Found |
|---|---|---|
| P (%) | 8.37 | 8.50 |
| S (%) | 8.64 | 8.86 |
| Cl (%) | 8.58 | 9.07 |

EXAMPLE 13

27.5 g. (0.1 mole) of a sodium salt of O-ethyl-O-2-chlorophenyl-phosphorothioate, which had been obtained in the same manner as in Example 1, was dissolved in 100 ml. of ethyl alcohol. To the solution, 18.5 g. (0.1 mole) of 2-phenylethyl bromide and a catalytic amount of potassium iodide were added at room temperature, and the mixture was refluxed with stirring for 5 hours. Subsequently, the reaction mixture was treated in the same manner as in Example 1 to obtain 32.5 g. of pale yellow, oily O-ethyl-O-2-chlorophenyl-S-2-phenylethyl phosphorothiolate, $n_D^{29.5}$ 1.5613; yield 91.2%.

Elementary analysis for $C_{16}H_{18}ClO_3PS$:

|  | Calculated | Found |
|---|---|---|
| P (%) | 8.68 | 8.80 |
| S (%) | 8.99 | 9.22 |
| Cl (%) | 9.94 | 9.68 |

EXAMPLE 14

6.7 g. (0.12 mole) of potassium hydroxide was dissolved in 50 ml. of ethyl alcohol. The solution was saturated with hydrogen sulfide to form an ethyl alcohol solution of potassium hydrosulfide. To this solution, 37.8 g. (0.12 mole) of O,O-diethyl-O-2,4-dichlorophenylthionophosphate was added, and the mixture was refluxed with stirringofr 4 hours. After cooling to room temperature, the mixture was charged with 22.2 g. (0.12 mole) of 2-phenylethyl bromide and was then refluxed with stirring for 4 hours. Subsequently, the reaction mixture was treated in the same manner as in Example 1 to obtain 40.5 g. of a pale yellow, oily O-ethyl-O-2,4-dichlorophenyl-S-2-phenylethylphosphorothiolate, $n_D^{25}$ 1.5678; yield 86.2%.

Elementary analysis for $C_{16}H_{17}Cl_2O_3PS$:

|  | Calculated | Found |
|---|---|---|
| P (%) | 7.92 | 7.85 |
| S (%) | 8.19 | 8.33 |
| Cl (%) | 18.12 | 17.93 |

EXAMPLES 15 – 32

According to Examples 1 - 14, the compounds set forth in the table below were synthesized.

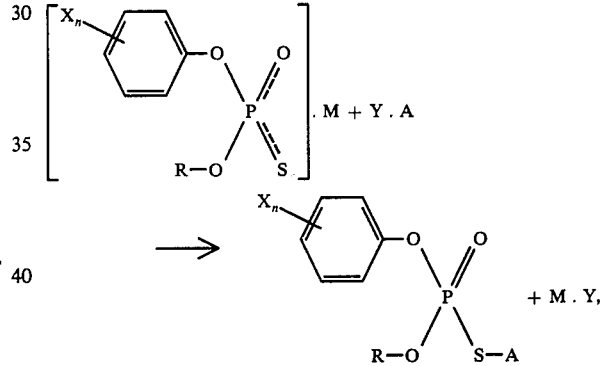

wherein A is a phenylethyl group.

Provided that the starting materials, salts of O-alkyl-O-substituted phenyl-phosphorothioates, were synthesized in the manner similar to that as in Example 11.

| Example No. | X_n-phenyl | R | H | Y | Solvent used | Reaction time and temperature | Yield | Refractive index | Elementary analysis | Calculated | Found |
|---|---|---|---|---|---|---|---|---|---|---|---|
| 15 | CH₃, Cl, CH₃ substituted | —C₂H₅ | K | Br | C₂H₅OH | 6 hrs. 80° C. | 84 % | $n_D^{30}$ 1.5570 | P<br>S<br>Cl | 8.05<br>8.33<br>9.21 | 7.89<br>8.23<br>8.96 |
| 16 | Cl, Cl, Cl substituted | ″ | ″ | ″ | ″ | ″ | 78 % | $n_D^{29}$ 1.5750 | P<br>S<br>Cl | 7.28<br>7.53<br>24.98 | 7.56<br>7.61<br>24.83 |

-continued

| Example No. | $X_n$-Ar- (aryl group) | R | H | Y | Solvent used | Reaction time and temperature | Yield | Refractive index | Elementary analysis Calculated | | Found |
|---|---|---|---|---|---|---|---|---|---|---|---|
| 17 | 2,4,5-trichlorophenyl | " | " | " | " | 8 hrs. 80° C. | 75 % | $n_D^{23}$ 1.5730 | P<br>S<br>Cl | 7.28<br>7.53<br>24.98 | 7.36<br>8.06<br>24.68 |
| 18 | pentachlorophenyl | " | " | " | " | 5 hrs. 80° C. | 70 % | $n_D^{23}$ 1.5830 | P<br>S<br>Cl | 6.26<br>6.48<br>35.84 | 6.66<br>6.68<br>35.89 |
| 19 | 4-(2-methylbutan-2-yl)phenyl (CH$_3$CH$_2$C(CH$_3$)$_2$-) | " | Na | " | H$_2$O | 5 hrs. 70° C. | 85 % | $n_D^{22}$ 1.5329 | P<br>S | 7.89<br>8.17 | 8.00<br>8.34 |
| 20 | 4-(pentan-2-yl)phenyl (CH$_3$CH$_2$CH$_2$CH(CH$_3$)-) | " | " | " | " | 6 hrs. 70° C. | 83 % | $n_D^{21.5}$ 1.5382 | P<br>S | 7.89<br>8.17 | 7.71<br>8.23 |
| 21 | 2-methyl-4-isopropylphenyl | " | K | " | C$_2$H$_5$OH | 5 hrs. 80° C. | 81 % | $n_D^{19}$ 1.5550 | P<br>S | 8.18<br>8.47 | 8.35<br>8.67 |
| 22 | 2,3,5-trimethylphenyl | " | " | " | " | " | 87 % | $n_D^{21}$ 1.5572 | P<br>S | 8.50<br>8.80 | 8.53<br>8.91 |
| 23 | 4-ethylphenyl (CH$_3$CH$_2$-) | " | Na | " | H$_2$O | 3 hrs. 70° C. | 90 % | $n_D^{21}$ 1.5561 | P<br>S | 8.84<br>9.15 | 8.79<br>9.23 |
| 24 | 3,4-dichloro-2,5-dimethylphenyl | " | K | " | C$_2$H$_5$OH | 8 hrs. 80° C. | 71 % | $n_D^{24}$ 1.5703 | P<br>S<br>Cl | 7.39<br>7.65<br>16.91 | 7.50<br>7.71<br>17.05 |
| 25 | 2-bromo-3,5-dimethylphenyl | " | " | " | " | " | 70 % | $n_D^{21}$ 1.5754 | P<br>S | 7.21<br>7.47 | 7.51<br>7.64 |
| 26 | 4-isopropylphenyl | " | " | " | H$_2$O | 4 hrs. 70° C. | 88 % | $n_D^{20}$ 1.5547 | P<br>S | 8.50<br>8.80 | 8.70<br>8.97 |
| 27 | 2,4-dimethylphenyl | " | Na | " | C$_2$H$_5$OH | 4 hrs. 80° C. | 86 % | $n_D^{21}$ 1.5531 | P<br>S | 8.84<br>9.15 | 8.90<br>9.38 |
| 28 | 2-methyl-4-isopropylphenyl (isomer) | " | K | " | " | 5 hrs. 80° C. | 82 % | $n_D^{19}$ 1.5554 | P<br>S | 8.18<br>8.47 | 8.32<br>8.50 |

-continued

| Example No. | $X_n$-phenyl R | H | Y | Solvent used | Reaction time and temperature | Yield | Refractive index | Elementary analysis Calculated | | Found |
| --- | --- | --- | --- | --- | --- | --- | --- | --- | --- | --- |
| 29 | CH₃, CH₃ (dimethylphenyl) | " | " | " | " | 83 % | $n_D^{22}$ 1.5533 | P<br>S | 8.84<br>9.15 | 8.79<br>9.13 |
| 30 | CH₃ (o.m.p: mixture) | " | Na | " | H₂O | 4 hrs. 70° C. | 88 % | $n_D^{24}$ 1.5530 | P<br>S | 9.21<br>9.53 | 9.27<br>9.65 |
| 31 | CH₃ (o-methylphenyl) | " | " | " | " | 5 hrs. 70° C. | 86 % | $n_D^{25}$ 1.5539 | P<br>S | 9.21<br>9.53 | 9.30<br>9.71 |
| 32 | Cl (chlorophenyl) | " | " | " | C₂H₅OH | 5 hrs. 80° C. | 84 % | $n_D^{25}$ 1.5620 | P<br>S<br>Cl | 8.68<br>8.99<br>9.94 | 8.72<br>9.08<br>10.24 |

EXAMPLE 33

6.7 g. (0.12 mole) of potassium hydroxide was dissolved in 50 ml. of ethyl alcohol. The solution was saturated with hydrogen sulfide to form an ethyl alcohol solution of potassium hydrosulfide. To this solution, 31.2 g. (0.12 mole) of O-diethyl-O-4-methylphenyl thionophosphate was added, and the mixture was refluxed with stirring for 5 hours. After removing ethyl alcohol from the reaction liquid by reduced pressure distillation, deposited crystals were suspended in ether, filtered and dried to obtain 29.2 g. of a potassium salt of O-ethyl-O-4-methylphenyl phosphorothioate, yield 90.1%; m.p. 157° – 160° C.

27.0 g. (0.1 mole) of this thiophosphate was dissolved in 100 ml. of acetone. To the solution, 7.7 g. (0.1 mole) of allyl chloride was added at room temperature, and the mixture was refluxed with stirring for 3 hours. After removing the solvent by distillation, the residue was charged with toluene, was washed with 5% sodium carbonate and was washed several times with water, and then the toluene layer was dried with anhydrous sodium sulfate. Subsequently, toluene was removed by reduced pressure distillation to obtain 25.4 g. of a pale yellow, oily O-ethyl-O-4-methylphenyl-S-allyl-phosphorothiolate, $n_D^{27.5}$ 1.5235; yield 93.3%.

Elementary analysis for $C_{12}H_{17}O_3PS$:

| | Calculated | Found |
| --- | --- | --- |
| P (%) | 11.37 | 11.45 |
| S (%) | 11.77 | 12.00 |

EXAMPLE 34

27.0 g. (0.1 mole) of a potassium salt of O-ethyl-O-4-methylphenyl-phosphorothioate, which had been prepared in the same manner as in Example 33, was dissolved in 100 ml. of ethyl alcohol. To the solution, 13.7 g. (0.1 mole) of sec-butyl bromide was added at room temperature, and the mixture was refluxed with stirring for 7 hours. Subsequently, the reaction mixture was treated in the same manner as in Example 33 to obtain 20.3 g. of a pale yellow, oily O-ethyl-O-4-methylphenyl-S-(sec)-butyl-phosphorothiolate, $n_D^{25}$ 1.5101; yield 70.5%.

Elementary analysis for $C_{13}H_{21}O_3PS$:

| | Calculated | Found |
| --- | --- | --- |
| P (%) | 10.74 | 10.57 |
| S (%) | 11.12 | 11.31 |

EXAMPLE 35

27.0 g. (0.1 mole) of a potassium salt of O-ethyl-O-4-methylphenyl phosphorothioate, which had been prepared in the same manner as in Example 33, was dissolved in 100 ml. of ethyl alcohol. To the solution, 11.9 g. (0.1 mole) of propargyl bromide was added, and the mixture was stirred at 60° – 70° C. for 4 hours. Subsequently, the reaction mixture was treated in the same manner as in Example 33 to obtain 24.9 g. of a pale brown, oily O-ethyl-O-4-methylphenyl-S-propargyl phosphorothiolate, $n_D^{28}$ 1.5285; yield 92.1%.

Elementary analysis for $C_{12}H_{15}O_3PS$:

| | Calculated | Found |
| --- | --- | --- |
| P (%) | 11.46 | 11.50 |
| S (%) | 11.86 | 11.93 |

EXAMPLE 36

O-Diethyl-O-4-(tert)-butylphenyl thionophosphate was treated in the same manner as in Example 35 to prepare white crystals of a potassium salt of O-ethyl-O-4-(tert)-butylphenyl phosphorothioate, yield 93.5%; m.p. 178° – 181° C.

31.2 g. (0.1 mole) of this thiophosphate was dissolved in 100 ml. of ethyl alcohol. To the solution, 12.1 g. (0.1 mole) of allyl bromide was added, and the mixture was stirred at 60° – 70° C. for 3 hours. Subsequently, the reaction mixture was treated in the same manner as in Example 33 to obtain 29.7 g. of a yellow, oily O-ethyl-O-4-(tert)-butylphenyl-S-allyl phosphorothiolate, $n_D^{29}$ 1.5179; yield 94.4%.

Elementary analysis for $C_{15}H_{23}O_3PS$:

|  | Calculated | Found |
|---|---|---|
| P (%) | 9.85 | 9.79 |
| S (%) | 10.20 | 10.37 |

EXAMPLE 37

6.7 g. (0.12 mole) of potassium hydroxide was dissolved in 50 ml. of ethyl alcohol. The solution was saturated with hydrogen sulfide to form an ethyl alcohol solution of potassium hydrosulfide. To this solution, 32.9 g. (0.12 mole) of O-diethyl-O-3,4-dimethylphenylthionophosphate was added, and the mixture was refluxed with stirring for 7 hours. After cooling to room temperature, the mixture was charged with 16.4 g. (0.12 mole) of sec-butyl bromide and a catalytic amount of potassium iodide, and was then refluxed with stirring for 9 hours. Subsequently, the reaction mixture was treated in the same manner as in Example 33 to obtain 26.7 g. of a pale brown, oily O-ethyl-O-3,4-dimethylphenyl-S-(sec-butyl phosphorothiolate, $n_D^{26}$ 1.5148; yield 73.6%.

Elementary analysis for $C_{14}H_{23}O_3PS$:

|  | Calculated | Found |
|---|---|---|
| P (%) | 10.24 | 10.41 |
| J (%) | 10.60 | 10.33 |

EXAMPLE 38

O,O-Diethyl-O-3,4-dimethylphenyl-thionophosphate was treated in the same manner as in Example 33 to prepare white crystals of a potassium salt of O-ethyl-O-3,4-dimethylphenyl-phosphorothioate, yield 90.5%; m.p. 170° – 172° C.

28.4 g. (0.1 mole) of this thiophosphate was dissolved in 100 ml. of ethyl alcohol. To the solution, 14.3 g. (0.1 mole) of 1-chloro-2-bromoethane was aded, and the mixture was refluxed with stirring for 10 hours. Subsequently, the reaction mixture was treated in the same manner as in Example 33 to obtain 22.0 g. of a pale brown, oily O-ethyl-O-3,4-dimethylphenyl-S-2-chloroethylphosphorothiolate, $n_D^{29.5}$ 1.5330; yield 71.1%.

Elementary analysis for $C_{12}H_{18}ClO_3PS$:

|  | Calculated | Found |
|---|---|---|
| P (%) | 10.03 | 10.26 |
| S (%) | 10.38 | 10.41 |
| Cl (%) | 11.48 | 11.28 |

EXAMPLE 39

26.8 g. (0.1 mole) of a sodium salt of O-ethyl-O-3,4-dimethylphenyl-phosphorothioate, which had been prepared in the same manner as in Example 33, was dissolved in 100 ml. of acetone. To the solution, 7.7 g. (0.1 mole) of allyl chloride was added, and the mixture was refluxed with stirring for 3 hours. Subsequently, the reaction mixture was treated in the same manner as in Example 33 to obtain 27.5 g. of a pale brown, oily O-ethyl-O-3,4-dimethylphenyl-S-allyl-phosphorothiolate, $n_D^{29.5}$ 1.5270; yield 96.0%.

Elementary analysis for $C_{13}H_1O_3PS$:

|  | Calculated | Found |
|---|---|---|
| P (%) | 11.82 | 10.87 |
| S (%) | 11.20 | 11.42. |

EXAMPLE 40

27.0 g. (0.1 mole) of a potassium salt of O-ethyl-O-3-methylphenyl-phosphorothioate, which had been prepared in the same manner as in Example 33, was dissolved in 100 ml. of water. To the solution, 14.3 g. (0.1 mole) of 1-chloro-2-bromoethane was added, and the mixture was stirred at 70° – 80° C. for 6 hours. Subsequently, the reaction mixture was treated in the same manner as in Example 33 to obtain 21.1 g. of a pale yellow, oily O-ethyl-O-3-methylphenyl-S-2-chloroethyl-phosphorothiolate, $n_D^{28}$ 1.5260; yield 71.5%.

Elementary analysis for $C_{11}H_{16}ClO_3PS$:

|  | Calculated | Found |
|---|---|---|
| P (%) | 10.51 | 10.53 |
| S (%) | 10.88 | 11.02 |
| Cl (%) | 12.03 | 11.81 |

EXAMPLE 41

27.0 g. (0.1 mole) of a potassium salt of O-ethyl-O-3-methylphenyl-phosphorothioate, which had been prepared in the same manner as in Example 33, was dissolved in 100 ml. of ethyl alcohol. To the solution, 12.1 g. (0.1 mole) of allyl bromide was added, and the mixture was stirred at 60° – 70° C. for 3 hours. Subsequently, the reaction mixture was treated in the same manner as in Example 33 to obtain 25.6 g. of a pale yellow, oily O-ethyl-O-3-methylphenyl-S-allyl-phosphorothiolate, $n_D^{27.5}$ 1.5235; yield 94.1%.

Elementary analysis:

|  | Calculated | Found |
|---|---|---|
| P (%) | 11.37 | 11.52 |
| S (%) | 11.77 | 12.01 |

EXAMPLE 42

27.0 g. (0.1 mole) of a potassium salt of O-ethyl-O-3-methylphenyl-phosphorothioate, which had been prepared in the same manner as in Example 33, was dissolved in 100 ml. of ethyl alcohol. To the solution, 13.7 g. (0.1 mole) of sec-butyl bromide was added, and the mixture was refluxed with stirring for 5 hours. Subsequently, the reaction mixture was treated in the same manner as in Example 33 to obtain 21.4 g. of a pale brown, oily O-ethyl-O-3-methylphenyl-S-(sec)-butyl-phosphorothiolate, $n_D^{24}$ 1.5077; yield 74.1%.

Elementary analysis for $C_{13}H_{21}O_3PS$:

|  | Calculated | Found |
|---|---|---|
| P (%) | 10.74 | 10.81 |
| S (%) | 11.12 | 11/32 |

EXAMPLE 43

6.7 g. (0.12 mole) of potassium hydroxide was dissolved in 50 ml of ethyl alcohol. The solution was saturated with hydrogen sulfide to form an ethyl alcohol solution of potassium hydrosulfide. To this solution 33.7 g. (0.12 mole) of O,O-diethyl-O-4-chlorophenylthionophosphate was added, and the mixture was refluxed with stirring for 4 hours. After cooling to room temperature, the mixture was charged with 14.5 g. (0.12 mole) of allyl bromide and was stirred at 60°–70° C. for 3 hours. After removal of the solvent, the residue ws charged with toluene, was washed with 5% sodium carbonate and was then washed several times with water, and the toluene layer was dried with anhydrous sodium sulfate. Subsequently, toluene was removed by reduced pressure distillation to obtain 30.6 g. of a pale yellow, oily O-ethyl-O-4-chlorophenyl-S-allylphosphorothiolate, $n_D^{27}$ 1.5370; yield 87.0%.

Elementary analysis for $C_{11}H_{14}ClO_3PS$:

|  | Calculated | Found |
|---|---|---|
| P (%) | 10.58 | 10.65 |
| S (%) | 10.95 | 11.21 |
| Cl (%) | 12.11 | 12.03 |

EXAMPLE 44

29.1 g. (0.1 mole) of a potassium salt of O-ethyl-O-4-chlorophenyl phosphorothioate, which has been obtained in the same manner as in Example 33, was dissolved in 100 ml. of ethyl alcohol. To the solution, 33.7 g. (0.1 mole) of sec-butyl bromide and a catalytic amount of potassium iodide were added at room temperature, and the mixture was refluxed with stirring for 7 hours. Subsequently, the reaction mixture was treated in the same manner as in Example 33 to obtain 24.2 g. of a pale yellow, oily O-ethyl-O-4-chlorophenyl-3-sec-butyl phosphorothiolate, $n_D^{25}$ 1.5221; yield 78.5%.

Elementary analysis for $C_{12}H_{18}ClO_3PS$:

|  | Calculated | Found |
|---|---|---|
| P (%) | 10.03 | 10.25 |
| S (%) | 10.38 | 10.43 |
| Cl (%) | 11.40 | 11.58 |

EXAMPLE 45

29.1 g. (0.1 mole of a potassium salt of O-ethyl-O-4-chlorophenyl-phosphorothioate, which had been prepared in the same manner as in Example 33, was dissolved in 100 ml. of ethyl alcohol. To the solution, 14.3 g. (0.1 mole) of 2-chloro-1-bromoethane was added at room temperature, and the mixture was refluxed with stirring for 7 hours. Subsequently, the reaction mixture was treated in the same manner as in Example 33 to obtain 22.2 g. of a pale yellow, oil O-ethyl-O-4-chlorophenyl-S-2-chloroethyl-phosphorothiolate, $n_D^{27}$ 1.5332; yield 70.3%.

Elementaty analysis for $C_{10}H_{13}Cl_2O_3PS$:

|  | Calculated | Found |
|---|---|---|
| P (%) | 9.83 | 10.05 |
| S (%) | 10.17 | 10.41 |
| Cl (%) | 22.50 | 22.20 |

EXAMPLE 46

6.7 g. (0.12 mole) of potassium hydroxide was dissolved in 50 ml. of ethyl alcohol. The solution was saturated with hydrogen sulfide to form an ethyl alcohol solution of potassium hydrosulfide. To this solution, 33.7 g. (0.12 mole) of O,O-diethyl-O-2-chlorophenylthionophosphate was added, and the mixture was refluxed with stirring for 4 hours. After cooling to room temperature, the mixture was charged with 9.2 g. (0.12 mole) of allyl chloride and was then stirred at 60°–70° C. for 3 hours. Subsequently, the reaction mixture was treated in the same manner as in Example 33 to obtain 31.0 g. of a pale yellow, oily O-ethyl-O-2-chlorophenyl-S-allyl-phosphorothiolate, $n_D^{29.5}$ 1.5370; yield 88.2%.

Elementary analysis for $C_{11}H_{14}ClO_3PS$:

|  | Calculated | Found |
|---|---|---|
| P (%) | 10.58 | 10.66 |
| S (%) | 10.95 | 11.21 |
| Cl (%) | 12.11 | 12.19 |

EXAMPLE 47

O,O-Diethyl-O-chlorophenyl-thionophosphate was treated in the same manner as in Example 33 to prepare white crystals of a potassium salt of O-ethyl-O-2-chlorophenylphosphorothioate, yield 94.3%, m.p. 184°–186° C. 29.1 g. (0.1 mole) of this thiophosphate was dissolved in 100 ml. of ethyl alcohol. To the solution, 13.7 g. (0.1 mole) of secbutyl bromide was added at room temperature, and the mixture was refluxed with stirring for 7 hours. Subsequently, the reaction mixture was treated in the same manner as in Example 33 to obtain 23.0 g. of a pale brown, oily O-ethyl-O-2-chlorophenyl-S-sec-butyl-phosphorothiolate, $n_D^{29}$ 1.5215; yield 74.6%.

Elementary analysis for $C_{12}H_{18}ClO_3PS$:

|  | Calculated | Found |
|---|---|---|
| P (%) | 10.03 | 10.28 |
| S (%) | 10.38 | 10.52 |
| Cl (%) | 11.48 | 11.44 |

EXAMPLE 48

27.5 g. (0.1 mole) of a sodium salt of O-ethyl-O-2-chlorophenyl-phosphorothioate, which had been prepared in the same manner as in Example 33, was dissolved in 100 ml. of acetone. To the solution, 11.9 g. (0.1 mole) of propargyl bromide was added at room temperature, and the mixture was refluxed with stirring for 3 hours. Subsequently, the mixture was treated in the same manner as in Example 33 to obtain 26.7 g. of a pale yellow, oily O-ethyl-O-2-chlorophenyl-S-propargyl phosphorothiolate, $n_D^{29}$ 1.5420; yield 91.7%.

Elementary analysis for $C_{11}H_{12}ClO_3PS$:

|  | Calculated | Found |
|---|---|---|
| P (%) | 10.63 | 10.70 |
| S (%) | 11.03 | 11.12 |
| Cl (%) | 12.19 | 12.15 |

EXAMPLE 49

O,O-Diethyl-O-2,4-dichlorophenyl-thionophosphate was treated in the same manner as in Example 33 to obtain white crystals of a potassium salt of O-ethyl-O-2,4-dichlorophenyl-phosphorothioate, yield 96.2%; m.p. 173°–175° C.

32.5 g. (0.1 mole) of this thiophosphate was dissolved in 100 ml. of acetone. To the solution, 7.7 g. (0.1 mole)

of allyl chloride was added at room temperature, and the mixture was refluxed with stirring for 3 hours. Subsequently, the mixture was treated in the same manner as in Example 33 to obtain 29.6 g. of a pale yellow, oily O-ethyl-O-2,4-dichlorophenyl-S-allyl phosphorothiolate, $n_D^{27.5}$ 1.5460; yield 90.6%.

Elementary analysis for $C_{11}H_{13}Cl_2O_3PS$:

|  | Calculated | Found |
|---|---|---|
| P (%) | 9.47 | 9.54 |
| S (%) | 9.80 | 9.68 |
| Cl (%) | 21.67 | 21.50 |

EXAMPLE 50

32.5 g. (0.1 mole) of a potassium salt of O-ethyl-O-2,4-dichlorophenyl-phosphorothioate, which had been prepared in the same manner as in Example 33, was dissolved in 100 ml. of ethyl alcohol. To the solution, 13.7 g. (0.1 mole) of sec-butyl bromide was added at room temperature, and the mixture was refluxed with stirring for 7 hours. Subsequently, the mixture was treated in the same manner as in Example 33 to obtain 26.5 g. of a pale yellow, oily O-ethyl-O-2,4-dichlorophenyl-S-sec-butyl-phosphorothiolate, $n_D^{27}$ 1.5304; yield 77.1%.

Elementary analysis for $C_{12}H_{17}Cl_2O_3PS$:

|  | Calculated | Found |
|---|---|---|
| P (%) | 9.02 | 9.13 |
| S (%) | 9.34 | 9.26 |
| Cl (%) | 20.66 | 20.73 |

EXAMPLE 51

29.1 g. of a potassium salt of O-ethyl-O-4-chlorophenyl-phosphorothiolate, which has been prepared in the same manner as in Example 33, was dissolved in 50 ml. of water. The solution was heated to 50° C., and then 12.5 g. of 2-chloroethyl-ethylthioether was added dropwise thereto over a period of 1 hour. After the dropwise addition, the mixture was heated with stirring at 70° C. for 4 hours, was charged with 100 g. of toluene and was then separated. Subsequently, the same after-treatments as in Example 33 were effected to obtain a pale yellow, oily O-ethyl-O-4-chlorophenyl-S-2-ethylthio-ethyl-phosphorothiolate, $n_D^{26}$ 1.5467; yield 92.0%.

Elementary analysis for $C_{12}H_{18}ClO_3PS_2$:

|  | Calculated | Found |
|---|---|---|
| P (%) | 9.10 | 9.61 |
| S (%) | 18.50 | 19.20 |
| Cl (%) | 10.43 | 10.11 |

EXAMPLE 52

A mixture comprising 28.4 g. of a potassium salt of O-ethyl-O-3,4O-ethyl-O-
-dimethylphenyl-phosphorothioate, which has been prepared in the same manner as in Example 33, 100 ml. of ethanol, and 17.3 g. of 2-chloroethylphenyl-thioether was treated in the same manner as in Example 33 to obtain a yellow, oily O-ethyl-O-3,4-dimethyl-S-2-phenylthioethylphosphorothiolate, yield 86%.

Elementary analysis for $C_{16}H_{22}O_3PS_2$:

|  | Calculated | Found |
|---|---|---|
| P (%) | 8.12 | 8.38 |
| S (%) | 16.75 | 17.05 |

EXAMPLE 53

A mixture comprising 32.5 g. of a potassium salt of O-ethyl-O-2,4-dichlorophenyl-phosphorothioate, which had been prepared in the same manner as in Example 33, 100 ml. of ethanol, and 19.6 g. of N-chloromethyl-phthalimide was refluxed for 5 hours. Subsequently, the mixture was subjected to ordinary after-treatments to obtain a pale yellow, oily O-ethyl-O-2,4-dichlorophenyl-S-N-phthalimidemethyl-phosphorothiolate, yield 83%.

Elementary analysis for $C_{17}H_{14}Cl_2NO_5PS$:

|  | Calculated | Found |
|---|---|---|
| P (%) | 6.95 | 7.13 |
| S (%) | 7.17 | 7.26 |
| Cl (%) | 15.92 | 15.40 |
| N (%) | 3.14 | 3.03 |

EXAMPLE 54

A mixture comprising 31.9 g. of a potassium salt of O-ethyl-O-3,5-dimethyl-4-chlorophenyl-phosphorothioate, which had been prepared in the same manner as in Example 33, 50 ml. of ethanol, 50 ml. of water and 13.7 g. of sec-butyl bromide was reacted at 60° C. for 10 hours. Subsequently, the mixture was subjected to ordinary after-treatments to obtain a pale yellow, oily substance of O-ethyl-O-3,5-dimethyl-4-chlorophenyl-S-sec-butyl phosphorothiolate, yield 57%.

Elementary analysis for $C_{14}H_{22}ClO_3PS$:

|  | Calculated | Found |
|---|---|---|
| P (%) | 9.21 | 9.50 |
| S (%) | 9.51 | 9.53 |
| Cl (%) | 10.55 | 10.26 |

EXAMPLE 55

25.6 g. (0.1 mole) of a potassium salt of O-ethyl-O-phenyl-phosphorothioate, which had been prepared in the same manner as in Example 2, was dissolved in 100 ml. of ethyl alcohol. To the solution, 13.7 g. (0.1 mole) of secbutyl bromide and a catalytic amount of potassium iodide were added, and the mixture was refluxed with stirring for 6 hours. Subsequently, the mixture was treated in the same manner as in Example 33 to obtain 20.0 g. of a pale yellow, oily O-ethyl-O-phenyl-S-sec-butyl phosphorothiolate, $n_D^{29}$ 1.5100; yield 73.0%.

Elementary analysis:

|  | Calculated | Found |
|---|---|---|
| P (%) | 11.29 | 11.52 |
| S (%) | 11.69 | 11.36 |

EXAMPLES 56 –114

According to Examples 33 to 56, compounds shown in the table below were synthesized.

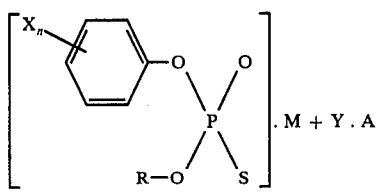

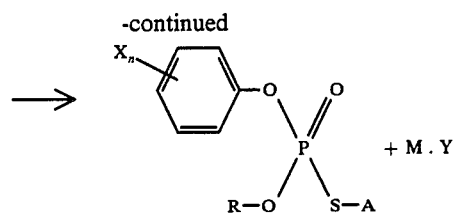

Provided that the starting materials, salts of O-alkyl-O-substituted phenyl phosphorothioates, were synthesized in entirely the same manner as in Example 33. The results of synthesis are shown in the table.

| Ex. No. | $X_n$— | A | R | M | Y | Solvent used | Reaction time and temperature | Yield | Refractive index | Elementary analysis Calculated | Found |
|---|---|---|---|---|---|---|---|---|---|---|---|
| 56 | CH$_3$—, Cl— (on phenyl) | —(Sec)C$_4$H$_9$ | —C$_2$H$_5$ | K | Br | C$_2$H$_5$OH | 7 hrs. 80° C. | 73 % | $n_D^{31}$ 1.5187 | P 9.60 S 9.93 Cl 10.98 | 9.55 9.91 11.12 |
| 57 | Cl, Cl (dichlorophenyl) | " | " | " | " | " | 8 hrs. 80° C. | 70 % | $n_D^{29}$ 1.5405 | P 8.20 S 8.49 Cl 28.16 | 8.33 8.18 28.30 |
| 58 | Cl, Cl, Cl (trichlorophenyl) | " | " | " | " | " | 10 hrs. 80° C. | 71 % | $n_D^{25}$ 1.5430 | P 8.20 S 8.49 Cl 28.16 | 8.17 8.71 28.64 |
| 59 | (CH$_3$)$_3$C—phenyl | " | " | " | " | " | 10 hrs. 80° C. | 73 % | $n_D^{24}$ 1.5078 | P 9.37 S 9.70 | 9.16 9.53 |
| 60 | Cl, Cl, Cl (trichlorophenyl) | —CH$_2$CH$_2$CH$_2$SC$_2$H$_5$ | " | Na | Cl | H$_2$O | 3 hrs. 60° C. | 87 % | $n_D^{24.5}$ 1.5490 | P 7.31 S 15.13 Cl 25.10 | 7.52 15.33 25.50 |
| 61 | Cl, Cl, Cl (trichlorophenyl) | —(n).C$_4$H$_9$ | " | K | Br | C$_2$H$_5$OH | 5 hrs. 70° C. | 86 % | $n_D^{21}$ 1.5444 | P 8.20 S 8.49 Cl 28.16 | 8.19 8.20 28.41 |
| 62 | CH$_3$CH$_2$—C(CH$_3$)$_2$—phenyl | —(Sec).C$_4$H$_9$ | " | " | " | " | 10 hrs. 80° C. | 72 % | $n_D^{22}$ 1.5064 | P 8.99 S 9.31 | 9.02 9.47 |
| 63 | CH$_3$, CH$_3$ (dimethylphenyl) | " | " | Na | " | " | 8 hrs. 80° C. | 78 % | $n_D^{20.5}$ 1.5138 | P 10.24 S 10.60 | 10.04 10.35 |
| 64 | CH$_3$CH$_2$CH$_2$CH(CH$_3$)—phenyl | " | " | K | " | " | 10 hrs. 80° C. | 73 % | $n_D^{21.5}$ 1.5031 | P 8.99 S 9.31 | 9.16 9.52 |
| 65 | (CH$_3$)$_2$CH—, CH$_3$ (phenyl) | " | " | " | " | " | 8 hrs. 80° C. | 73 % | $n_D^{19}$ 1.5170 | P 9.37 S 9.70 | 9.41 10.03 |
| 66 | CH$_3$, CH$_3$ (phenyl) | " | " | " | " | " | 8 hrs. 80° C. | 75 % | $n_D^{21}$ 1.5140 | P 10.24 S 10.60 | 10.43 10.81 |
| 67 | Cl (phenyl) | " | " | Na | " | " | 7 hrs. 80° C. | 78 % | $n_D^{22}$ 1.5220 | P 10.03 S 10.38 Cl 11.48 | 10.00 10.47 11.75 |

-continued

| Ex. No. | $X_n$-Ar | A | R | M | Y | Solvent used | Reaction time and temperature | Yield | Refractive index | Elementary analysis Calculated | Found |
|---|---|---|---|---|---|---|---|---|---|---|---|
| 68 | 3,4,5-Cl₃-C₆H₂- | —CH₂.CH=CH₂ | " | K | " | (CH₃)₂CO | 3 hrs. 60° C. | 93 % | $n_D^{21}$ 1.5561 | P 8.56<br>S 8.87<br>Cl 29.41 | 8.72<br>8.90<br>29.73 |
| 69 | 3,4,5-Cl₃-C₆H₂- | —CH₂CH₂.CH₂Cl | " | " | " | C₂H₅OH | 3 hrs. 80° C. | 90 % | $n_D^{24}$ 1.5525 | P 7.78<br>S 8.05<br>Cl 35.62 | 8.00<br>8.25<br>35.13 |
| 70 | 2,4,5-(CH₃)₃-C₆H₂- | —(Sec).C₄H₉ | " | " | " | " | 7 hrs. 80° C. | 75 % | $n_D^{25}$ 1.5239 | P 9.79<br>S 10.13 | 10.01<br>10.15 |
| 71 | 4-C₂H₅-C₆H₄- | " | " | " | " | " | 5 hrs. 80° C. | 78 % | $n_D^{25}$ 1.5018 | P 10.24<br>S 10.60 | 10.34<br>10.47 |
| 72 | 2,3-Cl₂-4,6-(CH₃)₂-C₆H- | " | " | " | " | " | 7 hrs. 80° C. | 72 % | $n_D^{25}$ 1.5422 | P 8.34<br>S 8.63<br>Cl 19.10 | 8.54<br>8.99<br>19.21 |
| 73 | 4-Br-2,5-(CH₃)₂-C₆H₂- | " | " | " | " | " | 7 hrs. 80° C. | 70 % | $n_D^{23}$ 1.5415 | P 8.12<br>S 8.41 | 8.03<br>8.52 |
| 74 | 2,4-(CH₃)₂-C₆H₃- | " | " | Na | " | " | 7 hrs. 80° C. | 76 % | $n_D^{25}$ 1.5107 | P 10.74<br>S 11.12 | 11.02<br>11.36 |
| 75 | 4-(iso-C₃H₇)-C₆H₄- | —(Sec).C₄H₉ | " | K | " | " | 6 hrs. 80° C. | 77 % | $n_D^{21}$ 1.5052 | P 9.79<br>S 10.13 | 10.01<br>10.15 |
| 76 | CH₃-C₆H₄- (o.m.p. mixture) | " | " | Na | " | " | 7 hrs. 80° C. | 80 % | $n_D^{24}$ 1.5112 | P 10.74<br>S 11.12 | 10.83<br>11.19 |
| 77 | 2,4-(CH₃)₂-C₆H₃- | " | " | " | " | " | 7 hrs. 80° C. | 76 % | $n_D^{21}$ 1.5135 | P 10.24<br>S 10.60 | 10.50<br>10.65 |
| 78 | 4-(iso-C₃H₇)-2,5-(CH₃)₂-C₆H₂- | " | " | K | " | " | 8 hrs. 80° C. | 76 % | $n_D^{21}$ 1.5181 | P 9.37<br>S 9.70 | 9.33<br>9.64 |
| 79 | 4-Cl-C₆H₄- | —CH₂CH₂CH₂Cl | " | " | " | " | 3 hrs. 80° C. | 94 % | $n_D^{21}$ 1.5341 | P 9.41<br>S 9.74<br>Cl 21.54 | 9.70<br>9.81<br>21.32 |
| 80 | 3,5-(CH₃)₂-C₆H₃- | —CH₂.CH₂.CH₂Cl | " | " | " | " | 3 hrs. 80° C. | 95 % | $n_D^{22}$ 1.5373 | P 9.59<br>S 9.93<br>Cl 10.98 | 9.79<br>10.21<br>11.00 |
| 81 | 4-Cl-3,5-(CH₃)₂-C₆H₂- | —CH₂.CH=CH₂ | " | " | " | (CH₃)₂CO | 3 hrs. 60° C. | 92 % | $n_D^{22}$ 1.5350 | P 9.65<br>S 9.99<br>Cl 11.05 | 10.05<br>10.23<br>11.28 |
| 82 | 2,4,5-Cl₃-C₆H₂- | " | " | " | " | " | 3 hrs. 60° C. | 90 % | $n_D^{21}$ 1.5560 | P 8.56<br>S 8.87<br>Cl 29.41 | 8.71<br>9.07<br>29.54 |

-continued

| Ex. No. | $X_n$-aryl | A | R | M | Y | Solvent used | Reaction time and temperature | Yield | Refractive index | Elementary analysis Calculated | Found |
|---|---|---|---|---|---|---|---|---|---|---|---|
| 83 | 2,4,5-tri-Cl-phenyl | $-CH_2 \cdot CH_2CH(CH_3)_2$ | " | " | " | $C_2H_5OH$ | 5 hrs. 80° C. | 87 % | $n_D^{20.5}$ 1.5462 | P 7.91 S 8.19 Cl 27.15 | 8.02 8.33 27.42 |
| 84 | 2,4,5-tri-Cl-phenyl | $(n)C_3H_7-$ | " | " | " | " | 4 hrs. 80° C. | 71 % | $n_D^{21.5}$ 1.5467 | P 8.52 S 8.82 Cl 29.25 | 9.09 8.98 28.97 |
| 85 | 2,4-di-Cl-phenyl | $(n)C_3H_7-$ | " | " | " | " | 5 hrs. 75° C. | 73 % | $n_D^{19.0}$ 1.5399 | P 9.41 S 9.74 Cl 21.54 | 9.27 9.86 21.64 |
| 86 | 2,4-di-CH$_3$-phenyl | " | " | " | " | " | 4 hrs. 78° C. | 79 % | $n_D^{20.0}$ 1.5200 | P 10.74 S 11.12 | 10.77 11.36 |
| 87 | 2-Cl-4,6-di-CH$_3$-phenyl | " | " | " | " | " | 5 hrs. 75° C | 73 % | $n_D^{18.5}$ 1.5315 | P 9.60 S 9.93 Cl 10.98 | 9.62 10.24 11.04 |
| 88 | 2,3,4,5-tetra-Cl-phenyl | " | " | " | " | $H_2O$ | 5 hrs. 75° C | 68 % | mp. 70.0–71.5° C. | P 7.16 S 7.41 Cl 40.99 | 7.13 7.12 41.31 |
| 89 | phenyl | " | " | " | " | 95% $C_2H_5OH$ | 5 hrs. 78° C. | 79 % | $n_D^{20.3}$ 1.5181 | P 11.96 S 12.32 | 11.98 12.73 |
| 90 | 3-CH$_3$-phenyl | " | " | " | " | 50 % $C_2H_5OH$ | 5 hrs. 75° C. | 74 % | $n_D^{25.5}$ 1.5151 | P 11.29 S 11.6 | 11.18 11.81 |
| 91 | 3,5-di-CH$_3$-phenyl | " | " | " | " | 95% $C_2H_5OH$ | 4 hrs. 78° C. | 71 % | $n_D^{23.0}$ 1.5152 | P 10.74 C 11.12 | 10.90 11.42 |
| 92 | 4-C$_2$H$_5$-phenyl | " | " | " | " | 40 % $C_2H_5OH$ | 5 hrs. 75° C. | 70 % | $n_D^{27.4}$ 1.5142 | P 10.74 S 11.12 | 10.75 11.50 |
| 93 | 4-tert-butyl-phenyl | " | " | " | " | 95 % $C_2H_5OH$ | 4.5 hrs. 78° C. | 78 % | $n_D^{23.5}$ 1.5102 | P 9.79 S 10.14 | 10.37 10.23 |
| 94 | 2-CH$_3$-4-Cl-phenyl | " | " | " | " | $C_2H_5OH$ | 4 hrs. 80° C | 74 % | $n_D^{23.0}$ 1.5271 | P 10.03 S 10.39 Cl 11.48 | 10.04 10.15 11.75 |
| 95 | 2,6-di-CH$_3$-3,5-di-Cl-phenyl | " | " | " | " | $H_2O$ | 5 hrs. 75° C. | 67 % | $n_D^{21.5}$ 1.5498 | P 8.67 S 8.98 Cl 19.85 | 8.56 8.94 20.21 |
| 96 | 4-Br-phenyl | " | " | " | " | 30 % $C_2H_5OH$ | 5 hrs. 70° C. | 69 % | $n_D^{20.0}$ 1.5438 | P 9.13 S 9.45 | 9.00 9.41 |
| 97 | 2-CH$_3$-phenyl | " | " | " | " | 50 % $C_2H_5OH$ | 5 hrs. 75° C. | 70 % | $n_D^{22.4}$ 1.5169 | P 11.29 S 11.69 | 11.52 12.36 |
| 98 | 4-CH$_3$-phenyl | " | " | Na | " | 50 % $C_2H_5OH$ | 5 hrs. 75° C. | 71 % | $n_D^{25.5}$ 1.5149 | P 11.29 S 11.69 | 11.08 11.73 |
| 99 | 2,4-di-CH$_3$-phenyl | " | " | K | " | 50 % $C_2H_5OH$ | 6 hrs. 70° C. | 65 % | $n_D^{18.4}$ 1.5182 | P 10.74 S 11.12 | 10.58 11.51 |

-continued

| Ex. No. | $X_n$-aryl | A | R | M | Y | Solvent used | Reaction time and temperature | Yield | Refractive index | Elementary analysis Calculated | Found |
|---|---|---|---|---|---|---|---|---|---|---|---|
| 100 | 2,4-(CH$_3$)$_2$-C$_6$H$_3$ | " | " | " | " | 50% C$_2$H$_5$OH | 6 hrs. 70° C. | 68% | $n_D^{18.5}$ 1.5192 | P 10.74 S 11.12 | 10.42 11.63 |
| 101 | 4-[C(CH$_3$)$_3$]-C$_6$H$_4$ | " | " | " | " | 70% C$_2$H$_5$OH | 5 hrs. 75° C. | 74% | $n_D^{18.5}$ 1.5146 | P 9.37 S 9.70 | 9.09 10.19 |
| 102 | 4-Cl-2,5-(CH$_3$)$_2$-C$_6$H$_2$ | " | " | " | " | 50% C$_2$H$_5$OH | 5 hrs. 75° C. | 75% | $n_D^{19.0}$ 1.5322 | P 9.60 S 9.93 Cl 10.98 | 9.41 9.86 11.05 |
| 103 | 2,5-Cl$_2$-4-CH$_3$-C$_6$H$_2$ | " | " | " | " | 30% C$_2$H$_5$OH | 5 hrs. 70° C. | 78% | $n_D^{20.0}$ 1.5392 | P 9.03 S 9.34 Cl 20.66 | 8.94 9.45 20.81 |
| 104 | 2-Cl-C$_6$H$_4$ | " | " | " | " | (CH$_3$)$_2$CO | 4.5 hrs. 55° C. | 72% | $n_D^{23.5}$ 1.5271 | P 10.51 S 10.88 Cl 12.03 | 10.36 11.06 12.00 |
| 105 | 3-Cl-C$_6$H$_4$ | " | " | " | " | C$_2$H$_5$OH | 5 hrs. 80° C. | 83% | $n_D^{20.0}$ 1.5270 | P 10.51 S 10.88 Cl 12.03 | 10.45 10.78 12.31 |
| 106 | 4-Cl-C$_6$H$_4$ | " | " | Na | " | 40% C$_2$H$_5$OH | 5 hrs. 73° C. | 72% | $n_D^{19.0}$ 1.5261 | P 10.51 S 10.88 Cl 12.03 | 10.60 10.70 12.21 |
| 107 | 2,6-Cl$_2$-C$_6$H$_3$ | " | " | K | " | 30% C$_2$H$_5$OH | 5 hrs. 70° C. | 81% | $n_D^{21.5}$ 1.5413 | P 9.41 S 9.74 Cl 21.54 | 9.50 9.78 21.72 |
| 108 | 2,4,5-Cl$_3$-C$_6$H$_2$ | " | " | " | " | (CH$_3$)$_2$CO | 5 hrs. 55° C. | 65% | $n_D^{22.0}$ 1.5470 | P 8.52 S 8.82 Cl 29.25 | 8.43 8.98 29.61 |
| 109 | 2,3,4,5-Cl$_4$-C$_6$H | " | " | " | " | H$_2$O | 4.5 hrs. 70° C. | 71% | $n_D^{27.5}$ 1.5603 | P 7.76 S 8.04 Cl 35.54 | 7.60 7.79 35.96 |
| 110 | 4-[C(CH$_3$)$_3$]-C$_6$H$_4$ | -(n)C$_4$H$_9$ | " | Na | " | C$_2$H$_5$OH | 5 hrs. 80° C. | 85% | $n_D^{27.0}$ 1.5041 | P 9.37 S 9.70 | 9.46 9.93 |
| 111 | 2,4,5-Cl$_3$-C$_6$H$_2$ | " | " | " | " | " | 5 hrs. 80° C. | 88% | $n_D^{26.5}$ 1.5409 | P 8.20 S 8.49 Cl 28.16 | 8.51 8.77 28.33 |
| 112 | 4-Cl-2,5-(CH$_3$)$_2$-C$_6$H$_2$ | " | " | " | " | " | 5 hrs. 80° C. | 90% | $n_D^{26.0}$ 1.5213 | P 9.21 S 9.51 Cl 10.55 | 9.29 9.66 10.48 |
| 113 | 4-Cl-2,5-(CH$_3$)$_2$-C$_6$H$_2$ | -(sec)C$_4$H$_9$ | " | " | " | " | 8 hrs. 80° C. | 68% | $n_D^{25.0}$ 1.5225 | P 9.21 S 9.51 Cl 10.55 | 9.43 9.72 10.67 |
| 114 | 4-Cl-C$_6$H$_4$ | -(n)C$_4$H$_9$ | " | " | " | " | 5 hrs. 80° C. | 89% | $n_D^{26.0}$ 1.5185 | P 10.03 S 10.38 Cl 11.48 | 10.32 10.51 11.62 |

Several processes for the formulation of the present compounds are exemplified below.

EXAMPLE 115

Formulation of emulsifiable concentrates:

Each of the compounds shown in the table below is thoroughly mixd with the solvent and emulsifier, in this order, in the proportions set forth in the table, whereby a homogeneous emulsifiable concentrate is obtained. In application, the emulsifiable concentrate is diluted with water, and the emulsion is sprayed.

| Active ingredient (%) | | Solvent (%) | | Emulsifier (%) | |
|---|---|---|---|---|---|
| Compound | (9) 50 | Xylene | 30 | Polyoxyethylene phenyl phenol polymer type | 20 |
| " | (17) 20 | Cyclo-hexanone | 50 | Polyoxyethylene alkylphenol type | 30 |

EXAMPLE 116

Formulation of wettable powders

40 Parts of the compound (5) is thoroughly mixed with 5 parts of emulsifier (Higher alcohol sodium sulfonate type). The mixture is added dropwise to 55 parts of 200 mesh talc under thorough stirring in a mortar and is kneaded therewith, whereby a wettable powder is obtained. In application, the wettable powder is diluted with water, and the solution is sprayed.

EXAMPLE 117

Each of the compounds shown in the table below is dissolved in a small amount of acetone and is thoroughly mixed with 200 mesh talc in proportions set forth in the table. Subsequently, acetone is removed by volatilization, whereby a dust is obtained.

In application, the dust is dusted as such.

| Active ingredient (%) | | Extender (%) | |
|---|---|---|---|
| Compound | (14) 2 | Talc | 98 |
| " | (16) 4 | " | 96 |

EXAMPLE 118

Formulation of granules

Each of the compounds shown in the table below is mixed with the binder and extender, in this order, in the proportions set forth in the table. The mixture is kneaded with a small amount of water, is formed into granules by means of a granulator and is then dried, whereby a granule is obtained. In application, the granule is sprinked as such

| Active ingredient (%) | | Binder (%) | | Extender (%) | |
|---|---|---|---|---|---|
| Compound | (16) 2 | Sodium lignosulfonate | 1 | Clay | 97 |
| " | (23) 5 | " | 2 | " | 93 |

What is claimed is:

1. A composition comprising an inert carrier and, as an active ingredient, an insecticidally or fungicidally effective amount of a phosphorothiolate represented by the formula,

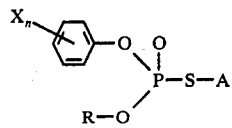

wherein R is an alkyl having up to 5 carbon atoms, A is an alkyl having 3 or 4 carbon atoms, haloalkyl having up to 3 carbon atoms, alkenyl having up to 4 carbon atoms, alkinyl having up to 4 carbon atoms, phenylthioalkyl having up to 9 carbon atoms, or phenylsubstituted etnyl X is hydrogen, a haogen or an alkyl having up to 5 atoms; and $n$ is an integer of 1 to 5.

2. A composition according to claim 1, wherein the composition is in a form of emulsifiable concentrate, wetable powder, oil spray, dust, ointment, granule, aerosol or fumigant.

3. A composition according to claim 1 wherein R is ethyl, and A is n-propyl, n-butyl, sec-butyl or 2-phenylethyl.

4. A composition according to claim 1 wherein R is an alkyl having up to 5 carbon atoms; A is phenyl substituted ethyl; X is hydrogen, halogen or alkyl having up to 5 carbon atoms; and n is an integer of 1 to 5.

5. A composition according to claim 1 wherein the formula is

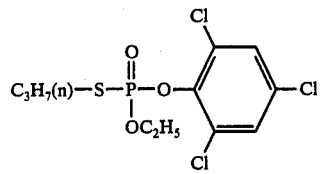

6. A composition according to claim 1 wherein the formula is

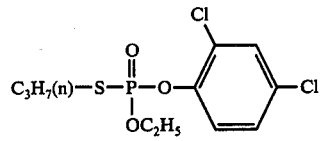

7. A composition according to claim 1 wherein the formula is

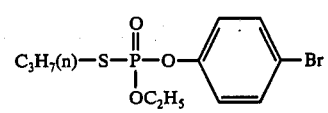

8. A composition according to claim 1 wherein the formula is

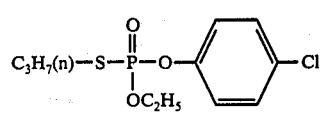

9. A composition according to claim 1 wherein the formula is

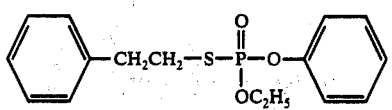

10. A composition according to claim 1 wherein the formula is

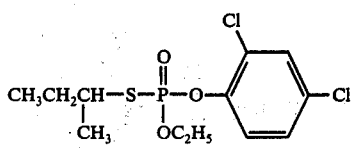

11. A composition according to claim 1 wherein the formula is

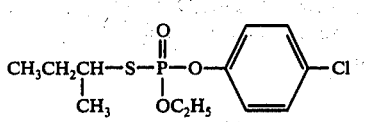

12. A composition according to claim 1 wherein the formula is

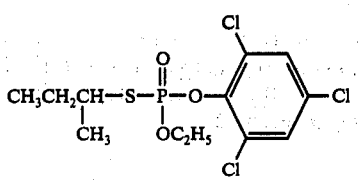

13. A composition according to claim 1 wherein the formula is

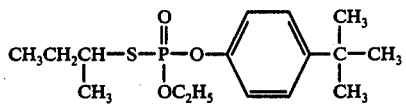

14. A composition according to claim 1 wherein the formula is

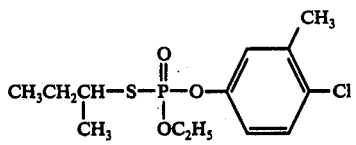

15. A composition according to claim 1 wherein the formula is

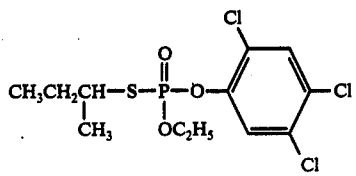

16. A composition according to claim 1 wherein the formula is

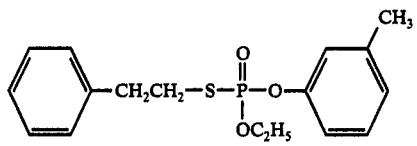

17. A composition according to claim 1 wherein the formula is

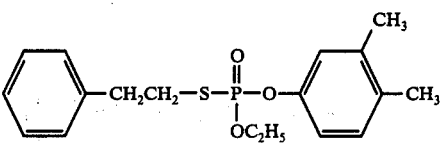

18. A composition according to claim 1 wherein the formula is

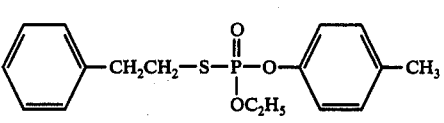

19. A composition according to claim 1 wherein the formula is

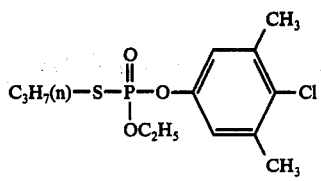

20. A composition according to claim 1 wherein the formula is

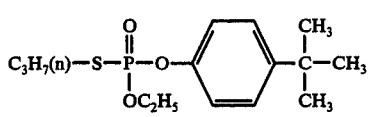

21. A composition according to claim 1 wherein the formula is

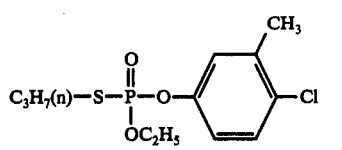

22. A composition according to claim 1 wherein the formula is

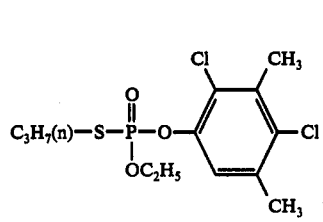

23. A composition according to claim 1 wherein the formula is

24. A composition according to claim 1 wherein the formula is

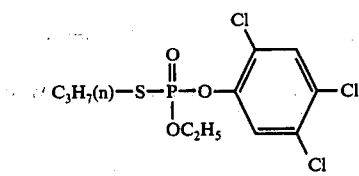

25. A composition according to claim 1 wherein the formula is

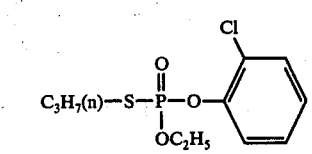

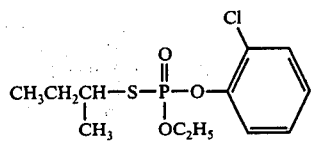

26. A composition according to claim 1 wherein the formula is

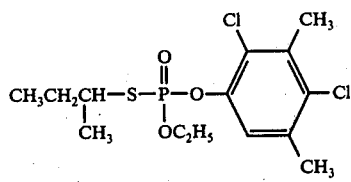

27. A composition comprising an inert carrier and, as an active ingredient, an insecticidally or fungicidally effective amount of a phosphorothiolate represented by the formula,

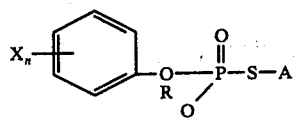

wherein R is an alkyl having up to 5 carbon atoms; A is alkylthioalkyl having up to 6 carbon atoms; X is hydrogen, halogen or alkyl having up to 5 carbon atoms; and n is an integer of 1 to 5.

* * * * *